US006919445B2

(12) United States Patent
Benson et al.

(10) Patent No.: US 6,919,445 B2
(45) Date of Patent: Jul. 19, 2005

(54) METHODS OF LABELLING POLYNUCLEOTIDES WITH DIBENZORHODAMINE DYES

(75) Inventors: Scott C. Benson, Alameda, CA (US); Joe Y. L. Lam, Castro Valley, CA (US); Steven Michael Menchen, Fremont, CA (US)

(73) Assignee: Applera Corporation, Foster City, CA (US)

( * ) Notice: Subject to any disclaimer, the term of this patent is extended or adjusted under 35 U.S.C. 154(b) by 0 days.

(21) Appl. No.: 10/441,950

(22) Filed: May 20, 2003

(65) Prior Publication Data

US 2004/0072209 A1 Apr. 15, 2004

Related U.S. Application Data

(60) Continuation of application No. 09/969,430, filed on Oct. 2, 2001, now Pat. No. 6,566,071, which is a division of application No. 09/784,943, filed on Feb. 14, 2001, now Pat. No. 6,326,153, which is a continuation of application No. 09/556,040, filed on Apr. 20, 2000, now Pat. No. 6,221,606, which is a division of application No. 09/199,402, filed on Nov. 24, 1998, now Pat. No. 6,111,116, which is a division of application No. 08/978,775, filed on Nov. 25, 1997, now Pat. No. 5,936,087.

(51) Int. Cl.[7] .......................... C12Q 1/68; C09B 69/00; C07D 311/78
(52) U.S. Cl. .......................... 536/26.6; 435/6; 435/91.5; 536/22.1; 536/25.3; 549/382
(58) Field of Search .................. 435/6, 91.5; 536/22.1, 536/25.3, 26.6; 549/382

(56) References Cited

U.S. PATENT DOCUMENTS

| | | | |
|---|---|---|---|
| 5,405,975 A | 4/1995 | Kuhn et al. | |
| 5,434,272 A | 7/1995 | Corrie et al. | |
| 5,750,409 A | 5/1998 | Herman et al. | |
| 5,936,087 A | 8/1999 | Benson et al. | |
| 6,008,379 A | 12/1999 | Benson et al. | |
| 6,020,481 A | 2/2000 | Benson et al. | |
| 6,051,719 A | 4/2000 | Benson et al. | |
| 6,080,868 A | 6/2000 | Lee et al. | |
| 6,111,116 A | 8/2000 | Benson et al. | |
| 6,130,101 A | 10/2000 | Mao et al. | |
| 6,221,606 B1 | 4/2001 | Benson et al. | |
| 6,248,884 B1 | 6/2001 | Lam et al. | |
| 6,326,153 B2 | 12/2001 | Benson et al. | |
| 6,566,059 B1 * | 5/2003 | Stanton et al. .................. | 435/6 |

FOREIGN PATENT DOCUMENTS

| | | |
|---|---|---|
| DE | 4137934 | 11/1991 |
| EP | 0543333 | 5/1993 |
| EP | 0805190 | 11/1997 |
| EP | 0940450 | 9/1999 |
| EP | 1054039 | 11/2000 |
| JP | 50040626 | 4/1975 |
| JP | 02050069 | 2/1990 |
| WO | WO 94/05688 | 3/1994 |
| WO | WO 00/58406 | 10/2000 |
| WO | WO 00/64988 | 11/2000 |

OTHER PUBLICATIONS

Arden et al., "Fluorescence and Lasing Properties of Rhodamine Dyes," *Jnl. of Luminescence* 48&49 : 352–358 (1991).

(Continued)

*Primary Examiner*—Zinna Northington Davis
(74) *Attorney, Agent, or Firm*—Alex Andrus; Vincent P Liptak; Vincent M Powers

(57) ABSTRACT

Dibenzorhodamine compounds having the structure

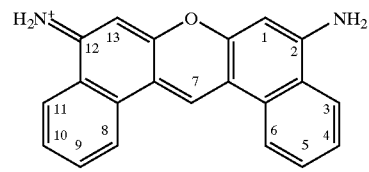

are disclosed, including nitrogen- and aryl-substituted forms thereof. In addition, two intermediates useful for synthesizing such compounds are disclosed, a first intermediate having the structure

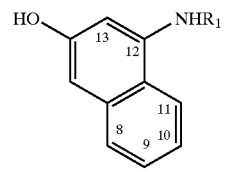

including nitrogen- and aryl-substituted forms thereof, and a second intermediate having the structure

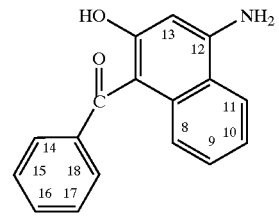

including nitrogen- and aryl-substituted forms thereof, wherein substituents at positions C-14 to C18 taken separately are selected from the group consisting of hydrogen, chlorine, fluorine, lower alkyl, carboxylic acid, sulfonic acid, —CH$_2$OH, alkoxy, phenoxy, linking group, and substituted forms thereof. The invention further includes energy transfer dyes comprising the dibenzorhodamine compounds, nucleosides labeled with the dibenzorhodamine compounds, and nucleic acid analysis methods employing the dibenzorhodamine compounds.

5 Claims, 7 Drawing Sheets

OTHER PUBLICATIONS

Arden–Jacob, Jutta; *Reihe Chemie*; Neue Langwellige Xanthen–Farbstoffe fur Fluoreszenzsonden und Farbstofflaser; Verlag Shaker, pub.; Prof. Dr. K.H. Drexhage and Prof. Dr. G. von Bunau, eds.; pps. 1–169 (1992).

Gee et al., "Novel Derivatization of Protein Thiols with Fluorinated Fluoresceins," *Tetrahedron Letters* 3(44): 7905–7908 (1996).

Haughland et al., "New Fluorescein, Rhodamine and Texa Red Analogs with Higher Fluorescence and Improved Photostability," Proceedings of the Xth International Congress, Histochemistry and Cytochemistry, pp. 273 (1996).

Lieberwirth et al., "Development of New Multiplex Dyes: Intramolecular Fluorescence Quenching of Rhodamine Dyes," *Jnl. of Fluorescence* 7(1): 59S–61S, 1997.

Onda et al., "Heterocycles. IV. Photolyses of the 4–Arylacetylated 1,2–Dihydroisoquinoline, Isocarbostyril and Its Enol Acetates," *Chemical and Pharmaceutical Bulletin* 25(11); 2935–2941 (1977).

Sauer et al., "New Fluorescent Dyes in the Red Region for Biodiagnostics," *Jnl. of Fluorescence, 5 (3)*:247–261 (1995).

Sauer et al., Physikalisch–Chemisches Institut, Heidelberg, Germany and Arden–Jacob et al., Institut for Physikalische Chemie, Siegen, Germany; "Design of Multiplex Dyes for the Detection of Different Biomolecules" 1995.

Sotomayor et al., "Bischler–Napieralski Cyclization–N/C–Alkylation Sequences for the Construction of Isoquinoline Alkaloids. Synthesis of Protoberberines and Benzo(c)phenanthridines via C–2'–Functionalized 3–Arylisoquinolines," *Journal of Organic Chemistry* 61(12): 4062–4072 (1996).

Sun et al., "Synthesis of Fluorinated Fluoresceins," *Journal of Organic Chemistry* 62(19): 6469–6475 (1997).

Takai, Hideyuki, "Electrophotographic Photoconductors," *Chemical Abstracts* 114(22): 743 (1991).

Tsunoda et al., "Naphthazolyphenyl Azides," *Chemical Abstracts* 83(14):75 (1975).

International Search Report from PCT/US98/24626 mailed May 10, 1999.

* cited by examiner

41

45

42

46

43

44

47

METHODS OF LABELLING POLYNUCLEOTIDES WITH DIBENZORHODAMINE DYES

This application is a continuation of application Ser. No. 09/969,430 filed Oct. 2, 2001 now U.S. Pat. No. 6,566,071 which is a division of application Ser. No. 09/784,943, filed Feb. 14, 2001 now U.S. Pat. No. 6,326,153, which is a continuation of application Ser. No. 09/556,040, filed Apr. 20, 2000, now U.S. Pat. No. 6,221,606, which is a division of application Ser. No. 09/199,402, filed Nov. 24, 1998, now U.S. Pat. No. 6,111,116, which is a division of application Ser. No. 08/978,775, filed Nov. 25, 1997, now U.S. Pat. No. 5,936,087, which are all incorporated herein by reference.

FIELD OF THE INVENTION

This invention relates generally to fluorescent dye compounds. More specifically, this invention relates to modified rhodamine dyes useful as fluorescent labeling reagents.

BACKGROUND

The non-radioactive detection of biological analytes utilizing fluorescent labels is an important technology in modem molecular biology. By eliminating the need for radioactive labels, safety is enhanced and the environmental impact and costs associated with reagent disposal is greatly reduced. Examples of methods utilizing such non-radioactive fluorescent detection include 4-color automated DNA sequencing, oligonucleotide hybridization methods, detection of polymerase-chain-reaction products, immunoassays, and the like.

In many applications it is advantageous to employ multiple spectrally distinguishable fluorescent labels in order to achieve independent detection of a plurality of spatially overlapping analytes, e.g., single-tube multiplex DNA probe assays and 4-color automated DNA sequencing methods. In the case of multiplex DNA probe assays, by employing spectrally distinguishable fluorescent labels, the number of reaction tubes may be reduced thereby simplifying experimental protocols and facilitating the production of application-specific reagent kits. In the case of 4-color automated DNA sequencing, multicolor fluorescent labeling allows for the analysis of multiple bases in a single lane thereby increasing throughput over single-color methods and reducing uncertainties associated with inter-lane electrophoretic mobility variations.

Assembling a set of multiple spectrally distinguishable fluorescent labels is problematic. Multi-color fluorescent detection imposes at least six severe constraints on the selection of dye labels, particularly for applications requiring a single excitation light source, an electrophoretic separation, and/or treatment with enzymes, e.g., automated DNA sequencing. First, it is difficult to find a set of structurally similar dyes whose emission spectra are spectrally resolved, since the typical emission band half-width for organic fluorescent dyes is about 40–80 nanometers (nm). Second, even if dyes with non-overlapping emission spectra are identified, the set may still not be suitable if the respective fluorescent quantum efficiencies are too low. Third, when several fluorescent dyes are used concurrently, simultaneous excitation becomes difficult because the absorption bands of the dyes are usually widely separated. Fourth, the charge, molecular size, and conformation of the dyes must not adversely affect the electrophoretic mobilities of the analyte. Fifth, the fluorescent dyes must be compatible with the chemistry used to create or manipulate the analyte, e.g., DNA synthesis solvents and reagents, buffers, polymerase enzymes, ligase enzymes, and the like. Sixth, the dye must have sufficient photostability to withstand laser excitation.

Currently available multiplex dye sets suitable in 4-color automated DNA sequencing applications require blue or blue-green laser light to adequately excite fluorescence emissions from all of the dyes making up the set, e.g., argon-ion lasers. Use of Blue or blue-green lasers in commercial automated DNA sequencing systems is disadvantageous because of the high cost and limited lifetime of such lasers.

SUMMARY

The present invention is directed towards our discovery of a class of dibenzorhodamine dye compounds suitable for the creation of sets of spectrally-resolvable fluorescent labels useful for multi-color fluorescent detection. The subject dye compounds are particularly well suited for use in automated 4-color DNA sequencing systems using an excitation light source having a wavelength greater than about 630 nm, e.g., a helium-neon gas laser or a solid state diode laser.

In a first aspect, the invention comprises dibenzorhodamine dye compounds having the structure

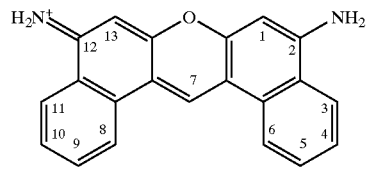

including nitrogen- and aryl-substituted forms thereof.

In a second aspect, the invention comprises intermediates useful for the synthesis of dibenzorhodamine compounds having the structure

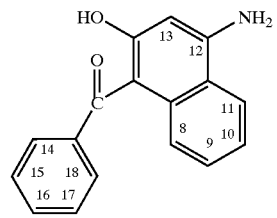

including nitrogen- and aryl-substituted forms thereof.

In a third aspect, the invention comprises intermediates useful for the synthesis of dibenzorhodamine compounds having the structure

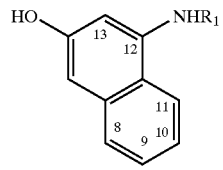

including nitrogen- and aryl-substituted forms thereof, wherein $R_1$ taken together with the C-12-bonded nitrogen and the C-12 and C-13 carbons forms a first ring structure having from 4 to 7 members; and/or $R_1$ taken together with the C-12-bonded nitrogen and the C-11 and C-12 carbons forms a second ring structure having from 5 to 7 members.

In a fourth aspect, the invention includes energy transfer dye compounds comprising a donor dye, an acceptor dye, and a linker linking the donor and acceptor dyes. The donor dye is capable of absorbing light at a first wavelength and emitting excitation energy in response, and the acceptor dye is capable of absorbing the excitation energy emitted by the donor dye and fluorescing at a second wavelength in response. The linker serves to facilitate the efficient transfer of energy between the donor dye and the acceptor dye. According to the present invention, at least one of the donor and acceptor dyes is a dibenzorhodamine dye having the structure set forth above.

In a fifth aspect, the present invention includes labeled nucleoside/tides having the structure

NUC—D wherein NUC is a nucleoside/tide or nucleoside/tide analog and D is a dibenzorhodamine dye compound having the structure set forth above. According to the invention, NUC and D are connected by a linkage wherein the linkage is attached to D at one of the substituent positions. Furthermore, if NUC comprises a purine base, the linkage is attached to the 8-position of the purine, if NUC comprises a 7-deazapurine base, the linkage is attached to the 7-position of the 7-deazapurine, and if NUC comprises a pyrimidine base, the linkage is attached to the 5-position of the pyrimidine.

In a sixth aspect, the invention includes polynucleotide analysis methods comprising the steps of forming a set of labeled polynucleotide fragments labeled with a dibenzorhodamine dye having the structure set forth above, subjecting the labeled polynucleotide fragments to a size-dependent separation process, e.g., electrophoresis, and detecting the labeled polynucleotide fragments subsequent to the separation process.

Various aspects of the above-described invention achieve one or more of the following important advantages over known fluorescent dye compounds useful for multiplex fluorescent detection: (1) the subject dye compounds may be efficiently excited by a low-cost red laser using wavelengths at or above 630 nm; (2) the emission spectra of the subject dye compounds can be modulated by minor variations in the type and location of nitrogen and/or aryl-substituents, allowing for the creation of dye sets having similar absorption characteristics yet spectrally resolvable fluorescence emission spectra; (3) the subject dye compounds may be easily attached to nucleosides/tides or polynucleotides without compromising their favorable fluorescence properties; (4) the subject dye compounds have narrow emission bandwidths, i.e., the emission bandwidth has a full-width at half the maximum emission intensity of below about 50 nm; (5) the subject dye compounds are highly soluble in buffered aqueous solution while retaining a high quantum yield; (6) the subject dye compounds are relatively photostable; and (7) the subject dye compounds have relatively large extinction coefficients, i.e., greater than about 50,000.

These and other features and advantages of the present invention will become better understood with reference to the following description, figures, and appended claims.

DETAILED DESCRIPTION OF THE PREFERRED EMBODIMENTS

Figure 1:
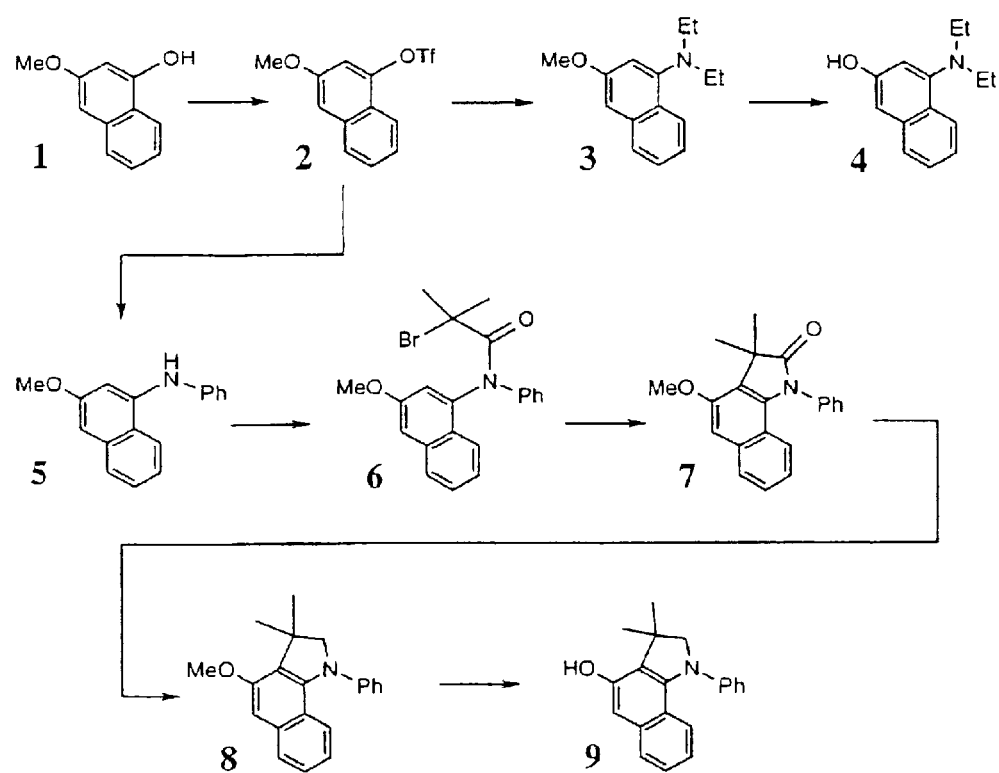
FIGS. 1–3 show exemplary synthetic pathways for the synthesis of the 1-amino-3-hydroxynapthalene intermediates of the invention.

Reference will now be made in detail to the preferred embodiments of the invention, examples of which are illustrated in the accompanying drawings. While the invention will be described in conjunction with the preferred embodiments, it will be understood that they are not intended to limit the invention to those embodiments. On the contrary, the invention is intended to cover all alternatives, modifications, and equivalents, which may be included within the invention as defined by the appended claims.

Generally, the present invention comprises a novel class of dibenzorhodamine dye compounds useful as fluorescent labels, methods and intermediates for synthesis of such dyes, reagents employing such dyes, and methods utilizing such dyes and reagents in the area of analytical biotechnology. The compounds of the present invention find particular application in the area of fluorescent nucleic acid analysis, e.g., automated DNA sequencing and fragment analysis, detection of probe hybridization in hybridization arrays, detection of nucleic acid amplification products, and the like.

I. Definitions

Unless stated otherwise, the following terms and phrases as used herein are intended to have the following meanings:

"Spectral resolution" in reference to a set of dyes means that the fluorescent emission bands of the dyes are sufficiently distinct, i.e., sufficiently non-overlapping, that reagents to which the respective dyes are attached, e.g. polynucleotides, can be distinguished on the basis of a fluorescent signal generated by the respective dyes using standard photodetection systems, e.g. employing a system of band pass filters and photomultiplier tubes, charged-coupled devices and spectrographs, or the like, as exemplified by the systems described in U.S. Pat. Nos. 4,230,558, 4,811,218, or in Wheeless et al, pgs. 21–76, in *Flow Cytometry: Instrumentation and Data Analysis* (Academic Press, New York, 1985).

"Electron-rich heterocycle" means cyclic compounds in which one or more ring atoms are not carbon, i.e., are hetero atoms, and the heteroatoms have unpaired electrons which contribute to a 6-π electronic system. Exemplary electron-rich heterocycles include but are not limited to pyrrole, indole, furan, benzofuran, thiophene, benzothiophene and other like structures.

"Linking group" means a moiety capable of reacting with a "complementary functionality" attached to a reagent or member of an energy transfer dye pair, such reaction forming a "linkage" connecting the dye to the reagent or member of the energy transfer dye pair. Preferred linking groups include isothiocyanate, sulfonyl chloride, 4,6-dichlorotriazinyl, succinimidyl ester, or other active carboxylate whenever the complementary functionality is amine. Preferably the linking group is maleimide, halo acetyl, or iodoacetamide whenever the complementary functionality is sulfhydryl. See R. Haugland, *Molecular Probes Handbook of Fluorescent Probes and Research Chemicals*, Molecular probes, Inc. (1992). In a particularly preferred embodiment, the linking group is a N-hydroxysuccinimidyl (NHS) ester and the complementary functionality is an amine, where to form the NHS ester, a dye of the invention including a carboxylate linking group is reacted with dicyclohexylcarbodiimide and N-hydroxysuccinimide.

"Substituted" as used herein refers to a molecule wherein one or more hydrogen atoms are replaced with one or more non-hydrogen atoms, functional groups or moieties. For example, an unsubstituted nitrogen is —NH$_2$, while a substituted nitrogen is —NHCH$_3$. Exemplary substituents include but are not limited to halo, e.g., fluorine and chlorine, lower alkyl, lower alkene, lower alkyne, sulfate, sulfonate, sulfone, amino, ammonium, amido, nitrile, lower alkoxy, phenoxy, aromatic, phenyl, polycyclic aromatic, electron-rich heterocycle water-solubilizing group, and linking group.

"Polycyclic aromatic" means aromatic hydrocarbons having multiple ring structures including biaryls and condensed benzenoid hydrocarbons. The biaryls are benzenoid compounds where two or more rings are linked together by a single bond. The parent system of this class is biphenyl. The condensed benzenoid compounds are characterized by two or more benzene rings fused together at ortho positions in such a way that each pair of rings shares two carbons. The simplest members of this group are napthalene, with two rings, and anthracene and phenanthrene, each with three rings.

"Lower alkyl" denotes straight-chain and branched hydrocarbon moieties containing from 1 to 8 carbon atoms, e.g., methyl, ethyl, propyl, isopropyl, tert-butyl, isobutyl, sec-butyl, neopentyl, tert-pentyl, and the like.

"Lower alkene" denotes a hydrocarbon containing from 1 to 8 carbon atoms wherein one or more of the carbon-carbon bonds are double bonds.

"Lower alkyne" denotes a hydrocarbon containing from 1 to 8 carbon atoms wherein one or more of the carbons are bonded with a triple bond.

"Nucleoside" refers to a compound consisting of a purine, deazapurine, or pyrimidine nucleoside base, e.g., adenine, guanine, cytosine, uracil, thymine, deazaadenine, deazaguanosine, and the like, linked to a pentose at the 1' position. When the nucleoside base is purine or 7-deazapurine, the sugar moiety is attached at the 9-position of the purine or deazapurine, and when the nucleoside base is pyrimidine, the sugar moiety is attached at the 1-position of the pyrimidine, e.g., Komberg and Baker, *DNA Replication*, 2nd Ed. (Freeman, San Francisco, 1992). The term "nucleotide" as used herein refers to a phosphate ester of a nucleoside, e.g., triphosphate esters, wherein the most common site of esterification is the hydroxyl group attached to the C-5 position of the pentose. The term "nucleoside/tide" as used herein refers to a set of compounds including both nucleosides and nucleotides. "Analogs" in reference to nucleosides/tides include synthetic analogs having modified base moieties, modified sugar moieties and/or modified phosphate moieties, e.g. described generally by Scheit, *Nucleotide Analogs* (John Wiley, New York, 1980). Phosphate analogs comprise analogs of phosphate wherein the phosphorous atom is in the +5 oxidation state and one or more of the oxygen atoms is replaced with a non-oxygen moiety. Exemplary analogs include but are not limited to phosphorothioate, phosphorodithioate, phosphoroselenoate, phosphorodiselenoate, phosphoroanilothioate, phosphoranilidate, phosphoramidate, boronophosphates, including associated counterions, e.g., H$^+$, NH$_4^+$, Na$^+$, if such counterions are present. Exemplary base analogs include but are not limited to 2,6-diaminopurine, hypoxanthine, pseudouridine, C-5-propyne, isocytosine, isoguanine, 2-thiopyrimidine, and other like analogs. Exemplary sugar analogs include but are not limited to 2'- or 3'-modifications where the 2'- or 3'-position is hydrogen, hydroxy, alkoxy, e.g., methoxy, ethoxy, allyloxy, isopropoxy, butoxy, isobutoxy and phenoxy, amino or alkylamino, fluoro, chloro and bromo. The term "labeled nucleoside/tide" refers to nucleosides/tides which are covalently attached to the dye compounds of Formula I through a linkage.

"Water solubilizing group" means a substituent which increases the solubility of the compounds of the invention in aqueous solution. Exemplary water-solubilizing groups include but are not limited to quaternary amine, sulfate, sulfonate, carboxylate, phosphate, polyether, polyhydroxyl, and boronate.

"Polynucleotide" or "oligonucleotide" means polymers of natural nucleotide monomers or analogs thereof, including double and single stranded deoxyribonucleotides, ribonucleotides, α-anomeric forms thereof, and the like. Usually the nucleoside monomers are linked by phosphodiester linkages, where as used herein, the term "phosphodiester linkage" refers to phosphodiester bonds or bonds including phosphate analogs thereof, including associated counterions, e.g., H$^+$, NH$_4^+$, Na$^+$, if such counterions are present. Polynucleotides typically range in size from a few monomeric units, e.g. 5–40, to several thousands of monomeric units. Whenever a polynucleotide is represented by a sequence of letters, such as "ATGCCTG," it will be understood that the nucleotides are in 5'->3' order from left to right and that "A" denotes deoxyadenosine, "C" denotes deoxycytidine, "G" denotes deoxyguanosine, and "T" denotes deoxythymidine, unless otherwise noted.

"Rhodamine dye" refers to dyes including the general polycyclic structure

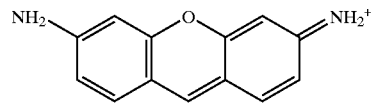

including any and all substituted versions thereof.

II. 1-Amino-3-Hydroxynapthalene Intermediates

A. Structure

In a first aspect, the present invention comprises a novel class of 1-amino-3-hydroxynapthalene compounds useful as intermediates in the synthesis of dibenzorhodamine dyes. These compounds have the general structure shown in Formula I immediately below, including substituted forms thereof, where R$_1$ taken together with the C-12-bonded nitrogen and the C-12 and C-13 carbons forms a first ring structure having from 4 to 7 members; and/or R$_1$ taken together with the C-12-bonded nitrogen and the C-11 and C-12 carbons forms a second ring structure having from 5 to 7 members. (Note that all molecular structures provided herein are intended to encompass not only the exact electronic structures presented, but also include all resonant structures, protonation states and associated counterions thereof.)

FORMULA I

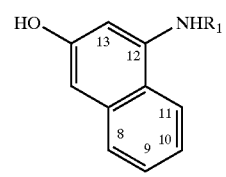

In the compound of Formula I, preferably the first ring structure has five members. More preferably, the five membered first ring structure includes one gem disubstituted carbon, e.g., wherein the gem substituents are lower alkyl, e.g., methyl. In an alternative preferred embodiment, the five membered ring is substituted with linking group or water-solubilizing group.

In another preferred embodiment of the intermediate of Formula I, the second ring structure has six members. More preferably, the six-membered second ring structure includes one gem disubstituted carbon, e.g., wherein the gem substituents are lower alkyl, e.g., methyl. In an alternative preferred embodiment, the five membered ring is substituted with linking group.

Preferably, the compound of Formula I includes one or more nitrogen substituents. Exemplary nitrogen substituents include but are not limited to lower alkyl, lower alkene, lower alkyne, phenyl, aromatic, electron-rich heterocycle, polycyclic aromatic, water-solubilizing group, and linking group, including substituted forms thereof. In a particularly preferred embodiment, the nitrogen substituents are lower alkyl and/or phenyl, including substituted forms thereof. More preferably, the nitrogen substituents are substituted lower alkyl or substituted phenyl, wherein the substituent is linking group, or water-solubilizing group.

In an additional preferred embodiment, one or more of carbons at positions C-8 to C-11 are substituted. Exemplary substituents include but are not limited to fluorine, chlorine, lower alkyl, lower alkene, lower alkyne, sulfate, sulfonate, sulfone, sulfonamide, sulfoxide, amino, ammonium, amido, nitrile, lower alkoxy, phenoxy, phenyl, polycyclic aromatic, electron-rich heterocycle, water-solubilizing group, and linking group, including substituted forms thereof. Preferably, one or more of the substituents is sulfonate.

Figure 2:
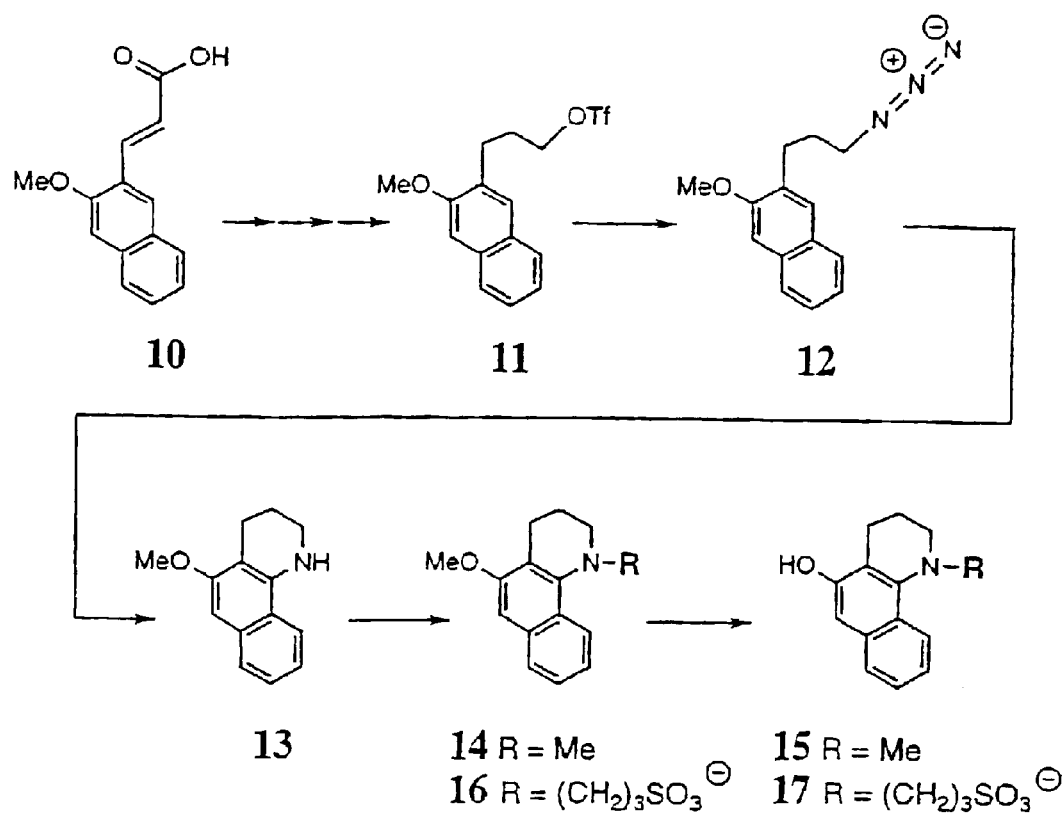
Figure 3:
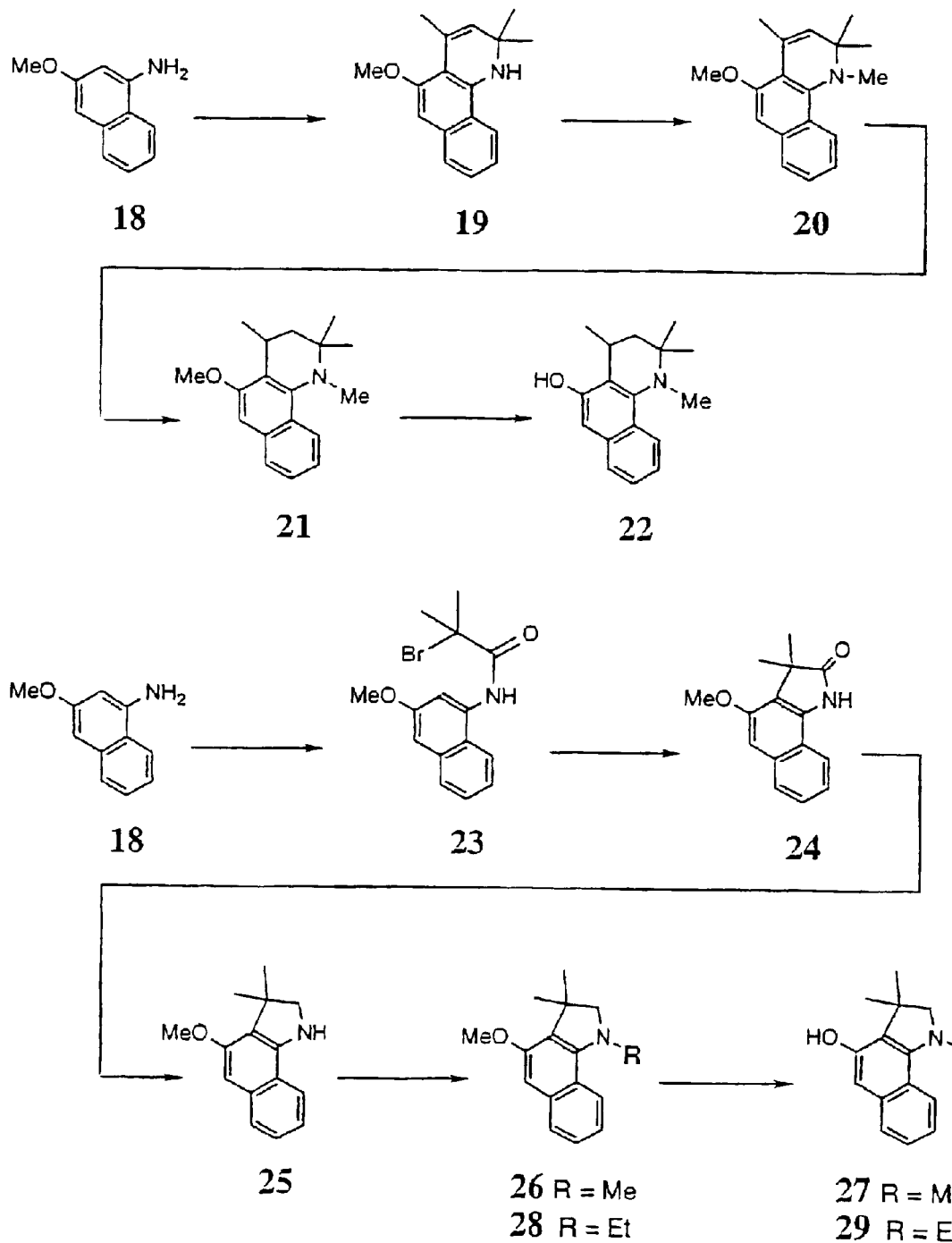

Several representative 1-amino-3-hydroxynapthalene compounds of the invention are shown in FIGS. 1–3, i.e., compounds 4, 9, 15, 17, 22, 27 and 29.

B. Synthetic Methods

Several synthetic methods are available for the synthesis of the 1-amino-3-hydroxynapthalene compounds described above, different methods being preferred depending on the nature of the ring structure and the nitrogen substituents of the particular compound to be synthesized.

A first preferred synthesis method suitable for the synthesis of 1-substituted-amino-3-hydroxynapthalene compounds, e.g., 1-diethylamino-3-hydroxynapthalene 4, is shown in FIG. 1. In this first method, a 3-methoxy-1-hydroxy napthalene 1 is reacted with dry triethylamine and trifluoromethanesulfonic anhydride to form a crude 3-methoxynapthalene-1-triflate 2. The triflate 2 is then reacted with an amine, e.g., a secondary amine, e.g., diethylamine, using palladium catalyzed triflate/amine coupling to form the substituted amine compound 3. Compound 3 is then deprotected using a boron tribromide deprotection procedure to produce the 1-amino-3-hydroxynapthalene product, e.g., 1-diethylamino-3-hydroxynapthalene 4. An example of this synthesis is provided in Example 1 below.

A second preferred synthesis method suitable for the synthesis of benzoindoline compounds, e.g., N-phenyl-3,3-dimethyl-4-hydroxy-benzoindoline 9, is also shown in FIG. 1. In this method, the 3-methoxynapthalene-1-triflate 2 is derivatized with a primary amine, e.g., aniline, using a palladium catalyzed triflate coupling reaction to give a secondary amine, e.g., 1-anilino-3-methoxynapthalene 5. The secondary amine 5 is acetylated using an acid chloride, e.g., an haloacetylchloride, to give a disubstituted amide, e.g., 1-amido-3-methoxynapthalene 6. The tertiary amide 6 is cyclized using a Lewis-acid-catalyzed Friedel-Crafts cyclization procedure to give compound 7, e.g., using $AlCl_3$. Compound 7 is than reduced, e.g., using LAH, to give compound 8. Subsequent methoxy group deprotection by a boron tribromide deprotection procedure gives the benzoindoline, e.g., N-phenyl-3,3-dimethyl-4-hydroxy-benzoindoline 9. An example of this synthesis is provided in Example 2 below.

A third preferred synthesis method suitable for the synthesis of N-substituted-5-hydroxy-(tetrahydro)benzoquinoline compounds, e.g., N-methyl-5-hydroxy-(tetrahydro)benzoquinoline 15, is shown in FIG. 2. In this method, compound 10 is synthesized from methoxynapthaldehyde by condensation with malonic acid using a piperidine catalyst in pyridine. Compound 10 is then reduced with hydrogen, followed by LAH reduction, and reacted with trifluoromethanesulfonic anhydride to give the triflate 11. The triflate 11 is reacted with $NaN_3$ to give compound 12. Compound 12 is complexed with a Lewis acid, e.g., $AlCl_3$, and refluxed yielding the cyclized benzoquinoline derivative 13. Next, a nitrogen substituent is added, e.g., the nitrogen is alkylated using a conventional alkylation procedure, e.g., the benzoquinoline derivative 13 is reacted with n-butyl lithium and an alkylating agent, e.g., MeI to give compound 14 or propane sultone to give compound 16. The methoxy group is then removed by a boron tribromide procedure giving a N-alkylbenzoquinoline derivative, e.g., compound 15 or 17. An example of this synthesis is provided in Example 3 below.

A fourth preferred synthesis method suitable for the synthesis of N-substituted-2,2,4-trimethyl-5-hydroxy-benzoquinoline compounds, e.g. N-methyl-2,2,4-trimethyl-5-hydroxy-(tetrahydro)benzoquinoline 22, is shown in FIG. 3. In this method, following the procedure of A. Rosowsky and E. J. Modest (J.O.C. 30 1832 1965, and references therein), 1-amino-3-methoxynapthalene 18 is reacted with acetone catalyzed by iodine and then quenched with saturated $Na_2S_2O_3$ to give the benzoquinoline compound 19. Compound 19 is then alkylated with an alkylating agent, e.g., MeI, according to a general alkylation procedure to give compound 20. The alkylated compound 20 is reduced with $H_2$ catalyzed by Pd/C to give a N-methyl-methoxyquinoline intermediate 21, and subsequent methoxy group deprotection by a general boron tribromide procedure yields the N-substituted-2,2,4-trimethyl-5-hydroxy-benzoquinoline compound, e.g., N-methyl-2,2,4-trimethyl-5-hydroxy-(tetrahydro)benzoquinoline 22. An example of this synthesis is provided in Example 4 below.

A fifth preferred general synthesis method suitable for the synthesis of N-substituted-3,3-dimethyl-4-hydroxy-benzoindoline compounds, e.g N-methyl-3,3-dimethyl-4-hydroxy-benzoindoline 27, is also shown in FIG. 3. In this method, a 1-amino-3-methoxynapthalene 18 is acetylated with an acid chloride, e.g., 2-bromo-2-methylpropionyl chloride, to give compound 23. Compound 23 is cyclized by reaction with $AlCl_3$ to give compound 24. Compound 24 is then reduced with LAH to give the 3,3-dimethyl-4-methoxybenzoindoline 25. Compound 25 is then alkylated with an alkylating agent, e.g., methyl iodide, to give a N-methyl-3,3-dimethyl-4-methoxybenzoindoline, e.g., compound 26. Subsequent methoxy group deprotection by with boron tribromide gives compound 27. An example of this synthesis is provided in Example 5 below.

III. Dibenzorhodamine Dye Compounds

A. Structure

In a second aspect, the present invention comprises a novel class of dibenzorhodamine dye compounds useful as molecular labels having the general structure shown in Formula II immediately below, including aryl- and nitrogen-substituted forms thereof.

FORMULA II

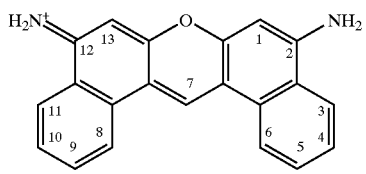

In one preferred embodiment of the compound of Formula II, the compound includes a first bridging group which when taken together with the C-12-bonded nitrogen and the C-12 and C-13 carbons forms a first ring structure having from 4 to 7 members, and/or a second bridging group which when taken together with the C-2-bonded-nitrogen and the C-1 and C-2 carbons forms a second ring structure having from 4 to 7 members. More preferably, one or both of the first and second ring structures has five members. In yet a more preferred embodiment, the five membered ring structure includes one gem disubstituted carbon, wherein the gem substituents are lower alkyl, e.g., methyl. In an alternative preferred embodiment, the five membered ring is substituted with linking group.

In another preferred embodiment, the compound of Formula II includes a C-7 substituent selected from the group consisting of acetylene, lower alkyl, lower alkene, cyano, phenyl, heterocyclic aromatic, electron-rich heterocycle, and substituted forms thereof. In a more preferred embodiment, the C-7 substituent is a phenyl or substituted phenyl having the structure

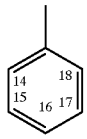

wherein aryl substituents at positions C-14 to C-18 taken separately may be selected from the group consisting of hydrogen, chlorine, fluorine, lower alkyl, carboxylic acid, sulfonic acid, —CH$_2$OH, alkoxy, phenoxy, linking group, and substituted forms thereof. Preferably, the phenyl substituent at C-18 is selected from the group consisting of carboxylic acid and sulfonate, and is most preferably carboxylic acid. In another preferred embodiment, substituents at positions C-14 and C-17 are chlorine. In yet another preferred embodiment, substituents at positions C-14 to C-17 are all chlorine or all fluorine. In a particularly preferred embodiment, substituents at one of positions C-15 and C-16 is linking group and the other is hydrogen, substituents at positions C-14 and C-17 are chlorine, and a substituent at position C-18 is carboxy.

In yet another preferred embodiment of the invention, the compound of Formula II includes one or more nitrogen substituents. Preferably, such substituents are selected from the group consisting of lower alkyl, lower alkene, lower alkyne, phenyl, aromatic, electron-rich heterocycle, polycyclic aromatic, water-solubilizing group, linking group, and substituted forms thereof. More preferably, the nitrogen substituents are selected from the group consisting of lower alkyl, phenyl, and substituted forms thereof, where exemplary substituents include linking group, and water-solubilizing group.

In another preferred embodiment of this second aspect of the invention, the compound of Formula II includes a third bridging group which when taken together with the C-12-bonded nitrogen and the C-11 and C-12 carbons forms a third ring structure having from 5 to 7 members, and/or a fourth bridging group which when taken together with the C-2-bonded nitrogen and the C-2 and C-3 carbons forms a fourth ring structure having from 5 to 7 members. Preferably, one or both of the third and fourth ring structures has six members. More preferably, the six membered ring structure includes one gem disubstituted carbon, wherein the gem substituents are lower alkyl, e.g., methyl.

In another preferred embodiment of the invention, the compound of Formula II includes aryl substituents at one or more of carbons C-1, C-3 through C-6, C-8 through C-11, and C-13. Exemplary aryl substituents include but are not limited to fluorine, chlorine, lower alkyl, lower alkene, lower alkyne, sulfate, sulfonate, sulfone, sulfonamide, sulfoxide, amino, ammonium, amido, nitrile, lower alkoxy, phenoxy, aromatic, phenyl, polycyclic aromatic, water-solubilizing group, electron-rich heterocycle, and linking group, including substituted forms thereof. In a particularly preferred embodiment, at least one substituent is sulfonate.

Figure 7:
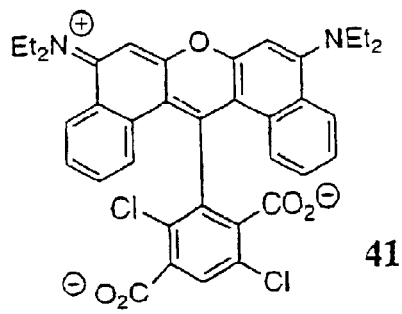
FIG. 7 shows the structures of several exemplary dibenzorhodamine dye compounds of the invention.
Figure 7:
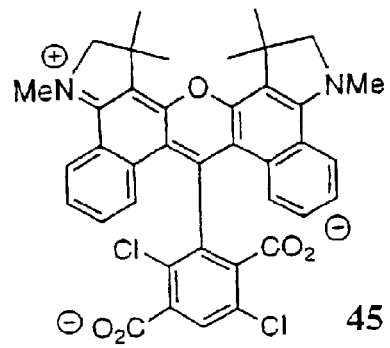
Figure 7:
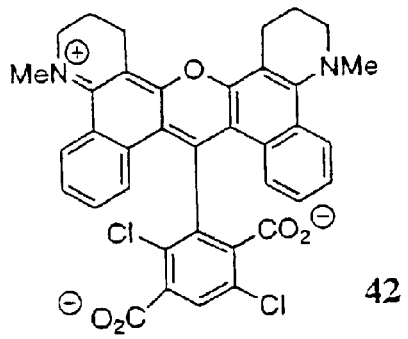
Figure 7:
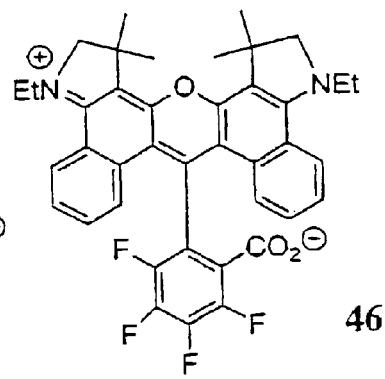
Figure 7:
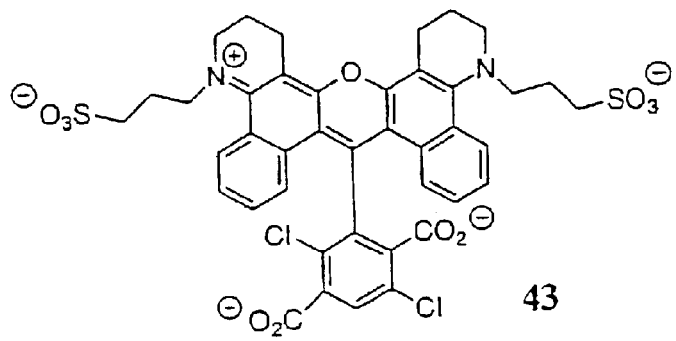
Figure 7:
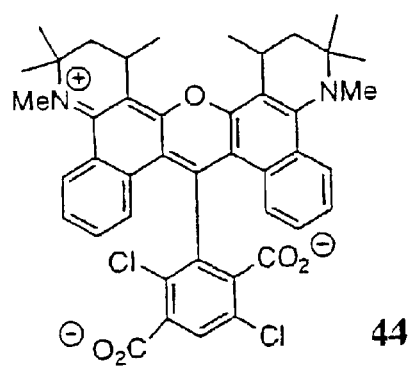
Figure 7:
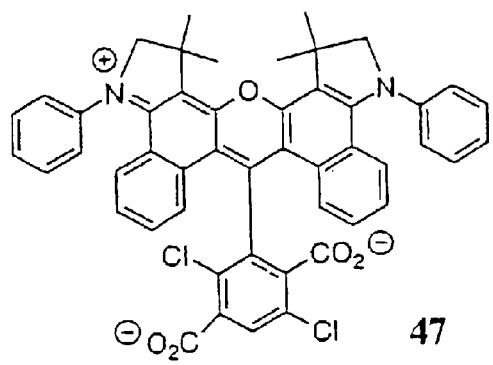

Several exemplary dye compounds according to this second aspect of the invention are shown in FIG. 7, i.e., compounds 41–47.

B. Synthetic Methods

Figure 4:
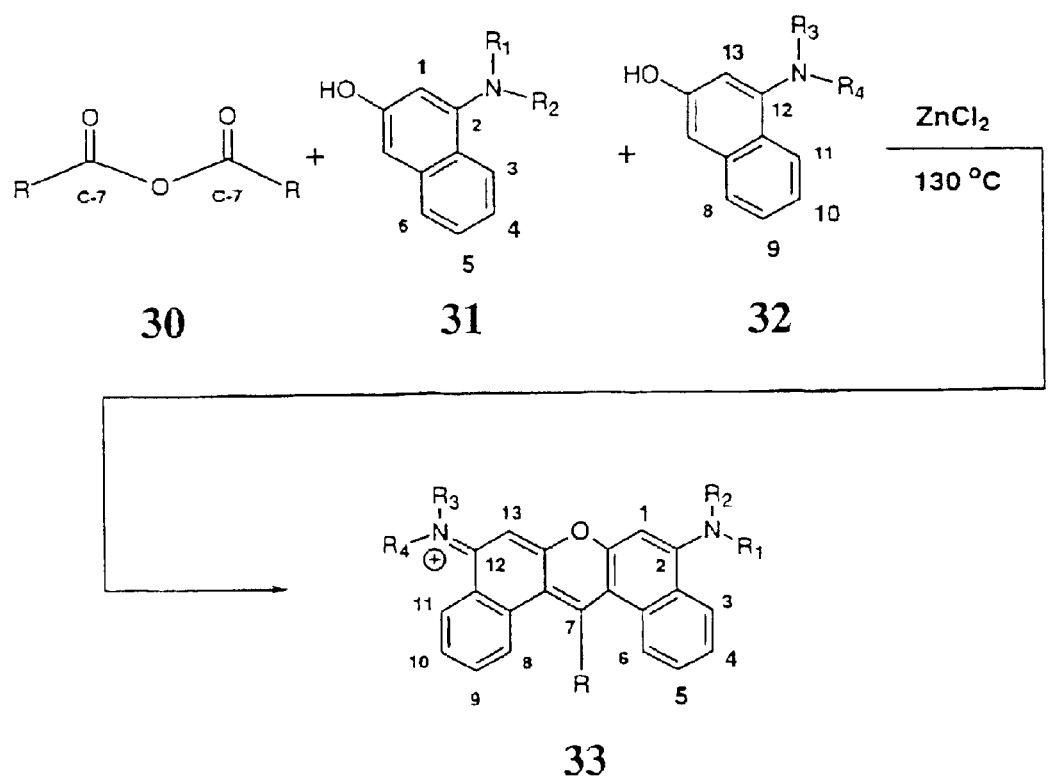
FIG. 4 shows a generalized synthetic pathway for the synthesis of the dibenzorhodamine dye compounds of the invention.

Generally, the dibenzorhodamine dyes of the present invention are synthesized as follows. See FIG. 4. An anhydride derivative 30, e.g., a phthalic anhydride, is mixed with 1-amino-3-methoxy intermediates 31 and 32, and Lewis acid, e.g., ZnCl$_2$, where the R-substituents in compound 30 may be the same or different, but are preferably the same. Exemplary R-substituents include but are not limited to acetylene, lower alkyl, lower alkene, phenyl, heterocyclic aromatic, electron-rich heterocycle, and substituted forms thereof. The mixture is heated briefly until melting is observed. A solvent, e.g., 1,2-dichlorobenzene, is added to the reaction mixture, and the heterogeneous mixture is heated to about 130° C. to about 180° C. The crude reaction mixture is cooled and purified by normal phase flash chromatography to yield dye compound 33. When the anhydride is part of a substituted phthalic anhydride, e.g., compound 34, two isomers are formed. See FIG. 5. The isomers 35 and 36 are separated by PTLC. The isomerically pure dyes are identified by single spots on normal and reverse phase TLC and by their UV/Visible absorption spectra and their long wavelength fluorescent excitation and emission spectra.

Figure 6:
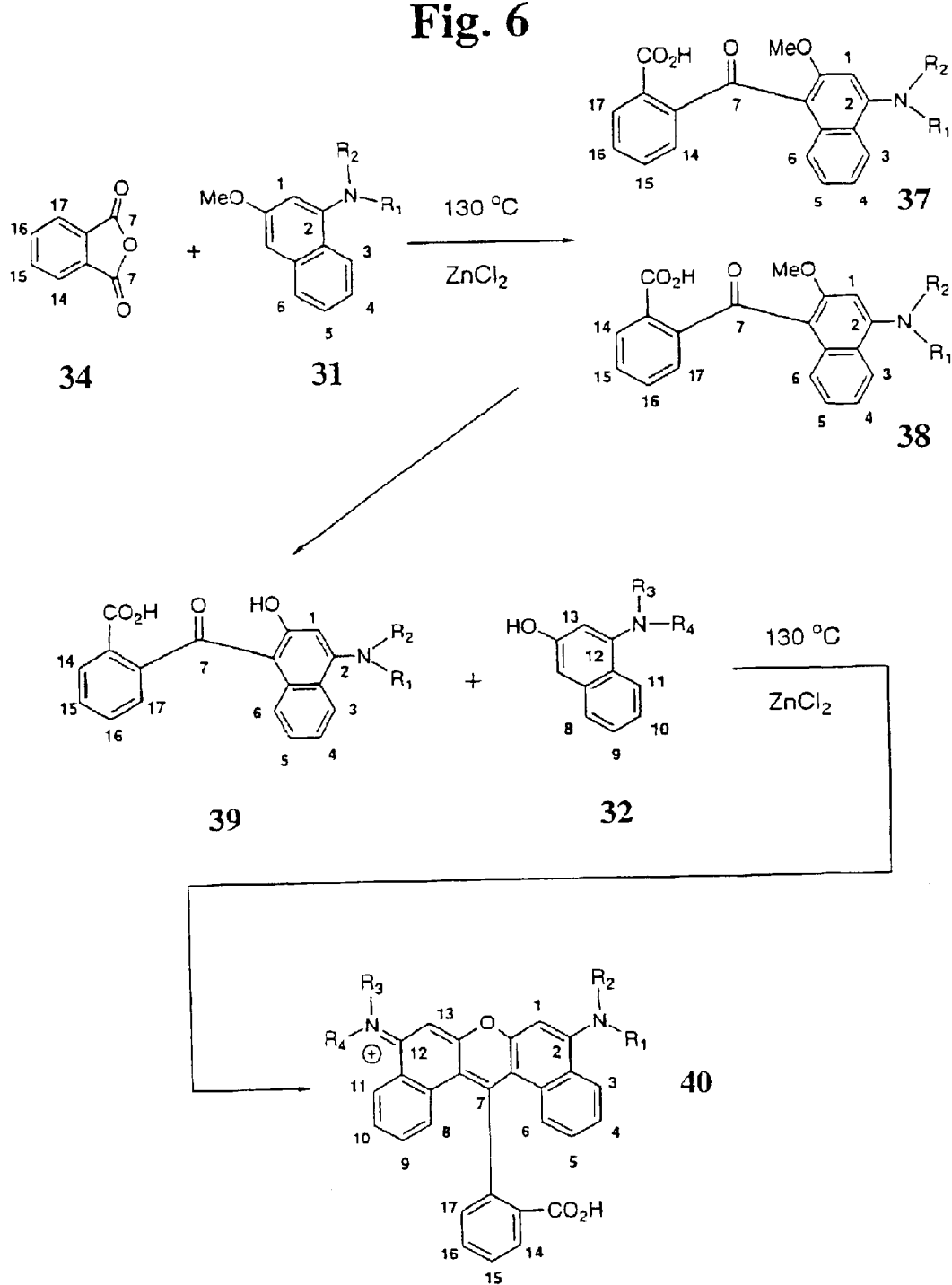

An alternative procedure for the synthesis of asymmetrical dye compounds is shown in FIG. 6. In this process, an anhydride derivative, e.g., phthalic anhydride 34, is mixed with dry nitrobenzene and heated. The mixture is cooled to room temperature and anhydrous AlCl$_3$ is added with stirring. Subsequently a 1-amino-3-methoxy intermediate 31 is added with stirring and the reaction is heated. The reaction is cooled and suspended in EtOAc. The organic layer is washed with saturated NH$_4$Cl, brine, dried over Na$_2$SO$_4$, filtered, and the solvent removed in vacuo. The resulting ketone intermediates 37/38 are purified and separated into distinct isomers 37 and 38 (except where substituents at C-14 and C-17 are the same and substituents at C-15 and C-16 are the same) by flash chromatography or recrystallization. The methoxy group of the isomerically pure ketone intermediate 37 or 38 is removed according to a general boron tribromide deprotection procedure to give the aminohydroxynapthalene ketone intermediate 39. Aminohydroxynapthalene ketone intermediate 39 is then reacted with a 1-amino-3-methoxy intermediate 32. The reaction is cooled, giving isomerically pure and asymmetrically substituted product 40 that may be further purified by PTLC.

V. Energy Transfer Dyes Incorporating the Dibenzorhodamine Dyes

In another aspect, the present invention comprises energy transfer dye compounds incorporating the dibenzorhodamine dye compounds of Formula I. Generally, the energy transfer dyes of the present invention include a donor dye which absorbs light at a first wavelength and emits excitation energy in response, an acceptor dye which is capable of absorbing the excitation energy emitted by the donor dye and fluorescing at a second wavelength in response, and a linker which attaches the donor dye to the acceptor dye, the linker being effective to facilitate efficient energy transfer between the donor and acceptor dyes. A through discussion of the structure, synthesis and use of such energy transfer dyes is provided by Lee et al., U.S. patent application Ser. No. 08/726,462, and Mathies et al., U.S. Pat. No. 5,654,419.

One linker according to the present invention for linking a donor dye to an acceptor dye in an energy transfer fluorescent dye has the general structure

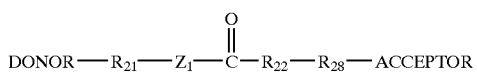

where $R_{21}$ is a lower alkyl attached to the donor dye, $Z_1$ is either NH, sulfur or oxygen, $R_{22}$ is a substituent which includes an alkene, diene, alkyne, a five and six membered ring having at least one unsaturated bond or a fused ring structure which is attached to the carbonyl carbon, and $R_{28}$ includes a functional group which attaches the linker to the acceptor dye.

In one embodiment of this linker, illustrated below, the linker has the general structure

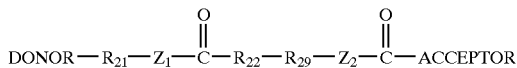

where $R_{21}$ and $R_{22}$ are as detailed above, $Z_1$ and $Z_2$ are each independently either NH, sulfur or oxygen, $R_{29}$ is a lower alkyl, and the terminal carbonyl group is attached to a ring structure of the acceptor dye. In the variation where $Z_2$ is nitrogen, the $C(O)R_{22}R_{29}Z_2$ subunit forms an amino acid subunit. Particular examples of five or six membered rings which may be used as $R_{22}$ in the linker include, but are not limited to cyclopentene, cyclohexene, cyclopentadiene, cyclohexadiene, furan, thiofuran, pyrrole, pyrazole, isoimidazole, pyran, pyrone, benzene, pyridine, pyridazine, pyrimidine, triazine, pyrazine and oxazine. Examples of fused ring structures include, but are not limited to indene, benzofuran, thionaphthene, indole and naphthalene. A preferred embodiment of this linker is where $R_{21}$ and $R_{29}$ are methylene, $Z_1$ and $Z_2$ are NH, and $R_{22}$ is benzene, as shown below.

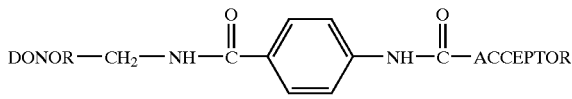

In another preferred embodiment of the energy-transfer-dye aspect of the present invention, the linker attaches to the dibenzorhodamine dye component of the energy transfer dye at the C-1 or 13 positions, or, alternatively, where the C-7 substituent is phenyl or substituted phenyl, at one of the C-15 or C-16 positions. In a particularly preferred embodiment, both members of the energy transfer pair are dibenzorhodamine dyes, and the first member is linked through the C-1 position and the second member is linked through one of the C-15 or C-16 positions.

In yet another preferred embodiment of the energy-transfer-dye aspect of the present invention, a first member the dye pair is a dibenzorhodamine dye, and a second member of the dye pair is cyanine, phthalocyanine, squaraine, bodipy, fluorescein, or dibenzorhodamine dye having different substitutions than the first member.

VI. Reagents Incorporating the Dibenzorhodamine Dyes

In another aspect, the present invention comprises reagents labeled with the dibenzorhodamine dye compounds of Formula I. Reagents of the invention can be virtually anything to which the dyes of the invention can be attached. Preferably, the dye is covalently attached to the reagent. Reagents may include but are not limited to proteins, polypeptides, polysaccharides, nucleotides, nucleosides, polynucleotides, lipids, solid supports, organic and inorganic polymers, and combinations and assemblages thereof, such as chromosomes, nuclei, living cells, such as bacteria or other microorganisms, mammalian cells, tissues, and the like.

A. Nucleoside/Tide Reagents

A preferred class of labeled reagents comprise nucleoside/tides that incorporate the dibenzorhodamine dyes of the invention. Such nucleoside/tide reagents are particularly useful in the context of labeling polynucleotides formed by enzymatic synthesis, e.g., nucleotide triphosphates used in the context of PCR amplification, Sanger-type polynucleotide sequencing, and nick-translation reactions.

Generally, the structure of the labeled nucleoside/tide reagent is

NUC—D                         FORMULA III where NUC is a nucleoside/tide or nucleoside/tide analog and D is a dibenzorhodamine dye compound of Formula II.

The linkage linking the nucleoside/tide and the dye may be attached to the dye at any one of substituent positions C-1 to C-18 or at a C-2 bonded nitrogen or a C-12 bonded nitrogen. Preferably, the dye includes a phenyl or substituted phenyl substituent at the C-7 position and is attached to the nucleoside/tide at one of the C-15 or C-16 substituent positions, the other position being a hydrogen atom.

When NUC includes a purine base, the linkage between NUC and D is attached to the $N^8$-position of the purine, when NUC includes a 7-deazapurine base, the linkage is attached to the $N^7$-position of the 7-deazapurine, and when NUC includes a pyrimidine base, the linkage is attached to the $N^5$-position of the pyrimidine.

Nucleoside labeling can be accomplished using any one of a large number of known nucleoside/tide labeling techniques employing known linkages, linking groups, and associated complementary functionalities. Generally, the linkage linking the dye and nucleoside should (i) not interfere with oligonucleotide-target hybridization, (ii) be compatible with relevant enzymes, e.g., polymerases, ligases, and the like, and (iii) not adversely affect the fluorescence properties of the dye. Exemplary base labeling procedures suitable for use in connection with the present invention include the following: Gibson et al, *Nucleic Acids Research*, 15:6455–6467 (1987); Gebeyehu et al, *Nucleic Acids Research*, 15: 4513–4535 (1987); Haralambidis et al, *Nucleic Acids Research*, 15: 4856–4876 (1987); Nelson et al., *Nucleosides and Nucleotides*, 5(3): 233–241 (1986); Bergstrom, et al.,*JACS*, 111: 374–375 (1989); and U.S. Pat. Nos. 4,855,225, 5,231,191, and 5,449,767.

Preferably, the linkages are acetylenic amido or alkenic amido linkages, the linkage between the dye and the nucleoside/tide base being formed by reacting an activated N-hydroxysuccinimide (NHS) ester of the dye with an alkynylamino- or alkenylamino-derivatized base of a nucleoside/tide. More preferably, the resulting linkage is 3-(carboxy)amino-1-propyn-1-yl having the structure

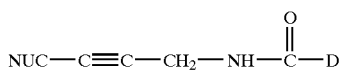

Alternative preferred linkages include substituted propargylethoxyamido linkages having the structure

NUC—C≡C—CH$_2$OCH$_2$CH$_2$NR$_3$X—D wherein X is selected from the group consisting of

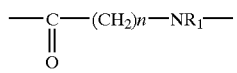

where n ranges from 1 to 5,

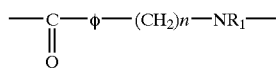

where n range from 1 to 5,

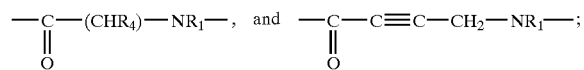

$R_1$ is selected from the group consisting of —H, lower alkyl and protecting group; and $R_3$ is selected from the group consisting of —H and lower alkyl. See Khan et al., U.S. patent application Ser. No. 08/833,854 filed Apr. 10, 1997.

The synthesis of alkynylamino-derivatized nucleosides is taught by Hobbs et al. in European Patent Application No. 87305844.0, and Hobbs et al., *J. Org. Chem.*, 54: 3420 (1989). Briefly, the alkynylamino-derivatized nucleotides are formed by placing the appropriate halodideoxynucleoside (usually 5-iodopyrimidine and 7-iodo-7-deazapurine dideoxynucleosides as taught by Hobbs et al. (cited above)) and Cu(I) in a flask, flushing with argon to remove air, adding dry DMF, followed by addition of an alkynylamine, triethyl-amine and Pd(0). The reaction mixture is stirred for several hours, or until thin layer chromatography indicates consumption of the halodideoxynucleoside. When an unprotected alkynylamine is used, the alkynylamino-nucleoside can be isolated by concentrating the reaction mixture and chromatographing on silica gel using an eluting solvent which contains ammonium hydroxide to neutralize the hydrohalide generated in the coupling reaction. When a protected alkynylamine is used, methanol/methylene chloride can be added to the reaction mixture, followed by the bicarbonate form of a strongly basic anion exchange resin. The slurry can then be stirred for about 45 minutes, filtered, and the resin rinsed with additional methanol/methylene chloride. The combined filtrates can be concentrated and purified by flash-chromatography on silica gel using a methanol-methylene chloride gradient. The triphosphates are obtained by standard techniques.

Particularly preferred nucleosides/tides of the present invention are shown below in Formula IV wherein

FORMULA IV

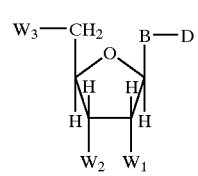

B is a nucleoside/tide base, e.g., uracil, cytosine, deazaadenine, or deazaguanosine; $W_1$ and $W_2$ taken separately are OH or a group capable of blocking polymerase-mediated template-directed polymerization, e.g., H, fluorine and the like; $W_3$ is OH, or mono-, di- or triphosphate or phosphate analog; and D is a dye compound of Formula I. In one particularly preferred embodiment, the nucleotides of the present invention are dideoxynucleotide triphosphates having the structure shown in Formula IV.1 below, including associated counterions if present.

FORMULA IV.1

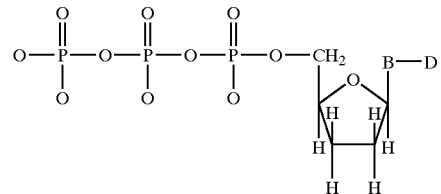

Labeled dideoxy nucleotides such as that shown in Formula IV.1 find particular application as chain terminating agents in Sanger-type DNA sequencing methods utilizing fluorescent detection.

In a second particularly preferred embodiment, the nucleotides of the present invention are deoxynucleotide triphosphates having the structure shown in Formula IV.2 below.

FORMULA IV.2

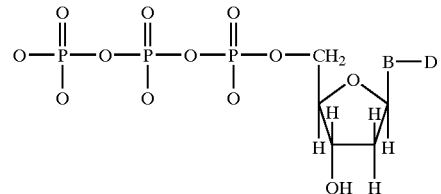

Labeled deoxynucleotides such as that shown in Formula IV.2 find particular application as reagents for labeling polymerase extension products, e.g., in the polymerase chain reaction or nick-translation.

B. Polynucleotide Reagents

Yet another preferred class of reagents of the present invention comprise polynucleotides labeled with the dibenzorhodamine dyes of the invention. Such labeled polynucleotides are useful in a number of important contexts including as DNA sequencing primers, PCR primers, oligonucleotide hybridization probes, oligonucleotide ligation probes, and the like.

In one preferred embodiment, the labeled polynucleotides of the present invention include multiple dyes located such that fluorescence energy transfer takes place between a donor dye and an acceptor dye. Such multi-dye energy-transfer polynucleotides find application as spectrally-tunable sequencing primers, e.g., Ju et al., *Proc. Natl. Acad.*

Sci. USA 92: 4347–4351 (1995), and as hybridization probes, e.g., Lee et al. *Nucleic Acids Research*, 21: 3761–3766 (1993).

Labeled polynucleotides may be synthesized either enzymatically, e.g., using a DNA polymerase or ligase, e.g., Stryer, *Biochemistry*, Chapter 24, W. H. Freeman and Company (1981), or by chemical synthesis, e.g., by the phosphoramidite method, the phosphite-triester method, and the like, e.g., Gait, *Oligonucleotide Synthesis*, IRL Press (1990). Labels may be introduced during enzymatic synthesis utilizing labeled nucleotide triphosphate monomers as described above, or introduced during chemical synthesis using labeled non-nucleotide or nucleotide phosphoramidites as described above, or may be introduced subsequent to synthesis.

Generally, if the labeled polynucleotide is made using enzymatic synthesis, the following procedure may be used. A template DNA is denatured and an oligonucleotide primer is annealed to the template DNA. A mixture of deoxynucleotide triphosphates is added to the mixture including dGTP, dATP, dCTP, and dTTP where at least a fraction of the deoxynucleotides is labeled with a dye compound of the invention as described above. Next, a polymerase enzyme is added under conditions where the polymerase enzyme is active. A labeled polynucleotide is formed by the incorporation of the labeled deoxynucleotides during polymerase-mediated strand synthesis. In an alternative enzymatic synthesis method, two primers are used instead of one, one primer complementary to the + strand and the other complementary to the − strand of the target, the polymerase is a thermostable polymerase, and the reaction temperature is cycled between a denaturation temperature and an extension temperature, thereby exponentially synthesizing a labeled complement to the target sequence by PCR, e.g., *PCR Protocols*, Innis et al. eds., Academic Press (1990).

Labeled polynucleotides may be chemically synthesized using the phosphoramidite method. Detailed descriptions of the chemistry used to form polynucleotides by the phosphoramidite method are provided elsewhere, e.g., Caruthers et al., U.S. Pat. Nos. 4,458,066 and 4,415,732; Caruthers et al., *Genetic Engineering*, 4: 1–17 (1982); *Users Manual Model* 392 *and* 394 *Polynucleotide Synthesizers*, pages 6-1 through 64-22, Applied Biosystems, Part No. 901237 (1991).

The phosphoramidite method of polynucleotide synthesis is the preferred method because of its efficient and rapid coupling and the stability of the starting materials. The synthesis is performed with the growing polynucleotide chain attached to a solid support, so that excess reagents, which are in the liquid phase, can be easily removed by filtration, thereby eliminating the need for purification steps between synthesis cycles.

The following briefly describes the steps of a typical polynucleotide synthesis cycle using the phosphoramidite method. First, a solid support including a protected nucleotide monomer is treated with acid, e.g., trichloroacetic acid, to remove a 5'-hydroxyl protecting group, freeing the hydroxyl for a subsequent coupling reaction. An activated intermediate is then formed by simultaneously adding a protected phosphoramidite nucleoside monomer and a weak acid, e.g., tetrazole, to the reaction. The weak acid protonates the nitrogen of the phosphoramidite forming a reactive intermediate. Nucleoside addition is complete within 30 s. Next, a capping step is performed which terminates any polynucleotide chains that did not undergo nucleoside addition. Capping is preferably done with acetic anhydride and 1-methylimidazole. The internucleotide linkage is then converted from the phosphite to the more stable phosphotriester by oxidation using iodine as the preferred oxidizing agent and water as the oxygen donor. After oxidation, the hydroxyl protecting group is removed with a protic acid, e.g., trichloroacetic acid or dichloroacetic acid, and the cycle is repeated until chain elongation is complete. After synthesis, the polynucleotide chain is cleaved from the support using a base, e.g., ammonium hydroxide or t-butyl amine. The cleavage reaction also removes any phosphate protecting groups, e.g., cyanoethyl. Finally, the protecting groups on the exocyclic amines of the bases and the hydroxyl protecting groups on the dyes are removed by treating the polynucleotide solution in base at an elevated temperature, e.g., 55° C.

Any of the phosphoramidite nucleoside monomers may be dye-labeled phosphoramidites as described above. If the 5'-terminal position of the nucleotide is labeled, a labeled non-nucleotidic phosphoramidite of the invention may be used during the final condensation step. If an internal position of the oligonucleotide is labeled, a labeled nucleotidic phosphoramidite of the invention may be used during any of the condensation steps.

Subsequent to synthesis, the polynucleotide may be labeled at a number of positions including the 5'-terminus, e.g., *Oligonucleotides and Analogs*, Eckstein ed., Chapter 8, IRL Press (1991) and Orgel et al., *Nucleic Acids Research* 11(18): 6513 (1983); U.S. Pat. No. 5,118,800; the phosphodiester backbone, e.g., ibid., Chapter 9; or at the 3'-terminus, e.g., Nelson, *Nucleic Acids Research* 20(23): 6253–6259, and U.S. Pat. Nos. 5,401,837 and 5,141,813. For a through review of oligonucleotide labeling procedures see R. Haugland in *Excited States of Biopolymers*, Steiner ed., Plenum Press, NY (1983).

In one preferred post-synthesis chemical labeling method an oligonucleotide is labeled as follows. A dye including a carboxy linking group is converted to the N-hydroxysuccinimide ester by reacting with approximately 1 equivalent of 1,3-dicyclohexylcarbodiimide and approximately 3 equivalents of N-hydroxysuccinimide in dry ethyl acetate for 3 hours at room temperature. The reaction mixture is washed with 5% HCl, dried over magnesium sulfate, filtered, and concentrated to a solid which is resuspended in DMSO. The DMSO dye stock is then added in excess (10–20×) to an aminohexyl derivatized oligonucleotide in 0.25 M bicarbonate/carbonate buffer at pH 9.4 and allowed to react for 6 hours, e.g., U.S. Pat. No. 4,757,141. The dye labeled oligonucleotide is separated from unreacted dye by passage through a size-exclusion chromatography column eluting with buffer, e.g., 0.1 molar triethylamine acetate (TEAA). The fraction containing the crude labeled oligonucleotide is further purified by reverse phase HPLC employing gradient elution.

VII. Methods Utilizing the Dibenzorhodamine Dyes

The dyes and reagents of the present invention are well suited to any method utilizing fluorescent detection, particularly methods requiring the simultaneous detection of multiple spatially-overlapping analytes. Dyes and reagents of the invention are particularly well suited for identifying classes of polynucleotides that have been subjected to a biochemical separation procedure, such as electrophoresis, or that have been distributed among locations in a spatially-addressable hybridization array.

In a preferred category of methods referred to herein as "fragment analysis" or "genetic analysis" methods, labeled polynucleotide fragments are generated through template-directed enzymatic synthesis using labeled primers or nucleotides, e.g., by ligation or polymerase-directed primer extension; the fragments are subjected to a size-dependent separation process, e.g., electrophoresis or chromatography; and, the separated fragments are detected subsequent to the separation, e.g., by laser-induced fluorescence. In a particularly preferred embodiment, multiple classes of polynucleotides are separated simultaneously and the different classes are distinguished by spectrally resolvable labels.

One such fragment analysis method known as amplified fragment length polymorphism detection (AmpFLP) is based on amplified fragment length polymorphisms, i.e., restriction fragment length polymorphisms that are amplified by PCR. These amplified fragments of varying size serve as linked markers for following mutant genes through families. The closer the amplified fragment is to the mutant gene on the chromosome, the higher the linkage correlation. Because genes for many genetic disorders have not been identified, these linkage markers serve to help evaluate disease risk or paternity. In the AmpFLPs technique, the polynucleotides may be labeled by using a labeled polynucleotide PCR primer, or by utilizing labeled nucleotide triphosphates in the PCR.

In another such fragment analysis method known as nick translation, a reaction is used to replace unlabeled nucleoside triphosphates in a double-stranded DNA molecule with labeled ones. Free 3'-hydroxyl groups are created within the unlabeled DNA by "nicks" caused by deoxyribonuclease I (DNAase I) treatment. DNA polymerase I then catalyzes the addition of a labeled nucleotide to the 3'-hydroxyl terminus of the nick. At the same time, the 5' to 3'-exonuclease activity of this enzyme eliminates the nucleotide unit from the 5'-phosphoryl terminus of the nick. A new nucleotide with a free 3'-OH group is incorporated at the position of the original excised nucleotide, and the nick is shifted along by one nucleotide unit in the 3' direction. This 3' shift will result in the sequential addition of new labeled nucleotides to the DNA with the removal of existing unlabeled nucleotides. The nick-translated polynucleotide is then analyzed using a separation process, e.g., electrophoresis.

Another exemplary fragment analysis method is based on variable number of tandem repeats, or VNTRs. VNTRs are regions of double-stranded DNA that contain adjacent multiple copies of a particular sequence, with the number of repeating units being variable. Examples of VNTR loci are pYNZ22, pMCT118, and Apo B. A subset of VNTR methods are those methods based on the detection of microsatellite repeats, or short tandem repeats (STRs), i.e., tandem repeats of DNA characterized by a short (2–4 bases) repeated sequence. One of the most abundant interspersed repetitive DNA families in humans is the (dC-dA)n—(dG-dT)n dinucleotide repeat family (also called the (CA)n dinucleotide repeat family). There are thought to be as many as 50,000 to 100,000 (CA)n repeat regions in the human genome, typically with 15–30 repeats per block. Many of these repeat regions are polymorphic in length and can therefore serve as useful genetic markers. Preferably, in VNTR or STR methods, label is introduced into the polynucleotide fragments by using a dye-labeled PCR primer.

In a particularly preferred fragment analysis method, classes identified in accordance with the invention are defined in terms of terminal nucleotides so that a correspondence is established between the four possible terminal bases and the members of a set of spectrally resolvable dyes. Such sets are readily assembled from the dyes of the invention by measuring emission and absorption bandwidths with commercially available spectrophotometers. More preferably, the classes arise in the context of the chemical or chain termination methods of DNA sequencing, and most preferably the classes arise in the context of the chain termination methods, i.e., dideoxy DNA sequencing, or Sanger-type sequencing.

Sanger-type sequencing involves the synthesis of a DNA strand by a DNA polymerase in vitro using a single-stranded or double-stranded DNA template whose sequence is to be determined. Synthesis is initiated at a defined site based on where an oligonucleotide primer anneals to the template. The synthesis reaction is terminated by incorporation of a nucleotide analog that will not support continued DNA elongation. Exemplary chain-terminating nucleotide analogs include the 2',3'-dideoxynucleoside 5'-triphosphates (ddNTPs) which lack the 3'-OH group necessary for 3' to 5' DNA chain elongation. When proper proportions of dNTPs (2'-deoxynucleoside 5'-triphosphates) and one of the four ddNTPs are used, enzyme-catalyzed polymerization will be terminated in a fraction of the population of chains at each site where the ddNTP is incorporated. If labeled primers or labeled ddNTPs are used for each reaction, the sequence information can be detected by fluorescence after separation by high-resolution electrophoresis. In the chain termination method, dyes of the invention can be attached to either sequencing primers or dideoxynucleotides. Dyes can be linked to a complementary functionality on the 5'-end of the primer, e.g. following the teaching in Fung et al, U.S. Pat. No. 4,757,141; on the base of a primer; or on the base of a dideoxynucleotide, e.g. via the alkynylamino linking groups disclosed by Hobbs et al, supra.

In each of the above fragment analysis methods labeled polynucleotides are preferably separated by electrophoretic procedures, e.g. Gould and Matthews, cited above; Rickwood and Hames, Eds., *Gel Electrophoresis of Nucleic Acids: A Practical Approach*, IRL Press Limited, London, 1981; Osterman, *Methods of Protein and Nucleic Acid Research*, Vol. 1 Springer-Verlag, Berlin, 1984; or U.S. Pat. Nos. 5,374,527, 5,624,800 and/or 5,552,028. Preferably the type of electrophoretic matrix is crosslinked or uncrosslinked polyacrylamide having a concentration (weight to volume) of between about 2–20 weight percent. More preferably, the polyacrylamide concentration is between about 4–8 percent. Preferably in the context of DNA sequencing in particular, the electrophoresis matrix includes a denaturing agent, e.g., urea, formamide, and the like. Detailed procedures for constructing such matrices are given by Maniatis et al., "Fractionation of Low Molecular Weight DNA and RNA in Polyacrylamide Gels Containing 98% Formamide or 7 M Urea," in *Methods in Enzymology*, 65: 299–305 (1980); Maniatis et al., "Chain Length Determination of Small Double- and Single-Stranded DNA Molecules by Polyacrylamide Gel Electrophoresis," *Biochemistry*, 14: 3787–3794 (1975); Maniatis et al., *Molecular Cloning: A Laboratory Manual*, Cold Spring Harbor Laboratory, New York, pgs. 179–185 (1982); and *ABI PRISM™ 377 DNA Sequencer User's Manual*, Rev. A, January 1995, Chapter 2 (p/n 903433, The Perkin-Elmer Corporation, Foster City, Calif.). The optimal electrophoresis conditions, e.g., polymer concentration, pH, temperature, concentration of denaturing agent, employed in a particular separation depends on many factors, including the size range of the nucleic acids to be separated, their base compositions, whether they are single stranded or double stranded, and the nature of the classes for which information is sought by electrophoresis. Accordingly application of the invention may require standard preliminary testing to optimize conditions for particular separations.

Subsequent to electrophoretic separation, the dye-polynucleotide conjugates are detected by measuring the fluorescence emission from the dye labeled polynucleotides. To perform such detection, the labeled polynucleotides are illuminated by standard means, e.g. high intensity mercury vapor lamps, lasers, or the like. Preferably the illumination means is a laser having an illumination beam at a wavelength above about 600 nm. More preferably, the dye-polynucleotides are illuminated by laser light generated by a He—Ne gas laser or a solid-state diode laser. The fluorescence is then detected by a light-sensitive detector, e.g., a photomultiplier tube, a charged coupled device, or the like. Exemplary electrophoresis detection systems are described elsewhere, e.g., U.S. Pat. Nos. 5,543,026; 5,274,240; 4,879,012; 5,091,652 and 4,811,218.

VIII. EXAMPLES

The invention will be further clarified by a consideration of the following examples, which are intended to be purely exemplary of the invention and not to in any way limit its scope.

Materials and Methods

All chemicals were purchased from Aldrich Chemical Company unless otherwise noted. Martius yellow was purchased from Fluka. Acetone was dried over $CaSO_4$ and distilled. Dichloromethane ($CH_2Cl_2$) and nitrobenzene were dried over $CaH_2$ and distilled. Tetrahydrofuran (THF) was dried over lithium aluminum hydride (LAH) and distilled as needed. Triethylamine ($Et_3N$) was dried over sodium and distilled. DMSO (99.9%) and N,N-diisopropylethylamine (99.5%) were dried and stored over activated molecular sieves. Silica gel (220–400 mesh) from VWR was used for normal phase flash chromatography. Reverse phase chromatography was performed on octadecyl functionalized silica gel from Aldrich. Preparative thin layer chromatography (PTLC) was performed on 1 and 2 mm pre-made silica gel plates from EM science (VWR). TLC was performed on aluminum back silica gel 60 plates from EM science (VWR). Developed spots were visualized with both long and short wavelength UV irradiation.

Absorption spectroscopy was performed on a Hewlett Packard model 8451A UV/Vis diode array spectrophotometer. Fluorescence measurements were made on a Perkin-Elmer LS-50B luminescence spectrophotometer. NMR spectra were determined on a Varian 300 MHz NMR referenced relative to a solvent peak at 7.26 ppm in $CD_3Cl$ or 3.31 ppm in $CD_3OD$. HPLC purification of oligomer labeled dye fragments was performed on a Perkin-Elmer Series 200 pump, employing a reverse phase C-18 column, with both UV and fluorescence emission detection. Fluorescence detection was performed by a Perkin-Elmer LC 240 fluorescence detector equipped with a red sensitive PMT, and UV detection was performed with a Model LC 295 UV/Vis detector. Pump and detectors were all interfaced with a Perkin-Elmer Model 1022 computer run in two-channel mode. Buffers were made up fresh from the following concentrated stock: 10×TBE (0.89 M tris-(hydroxymethyl) aminomethane, 0.89 M borate, 0.02 M ethylenediaminetetraacetic acid disodium salt), and 0.1 M TEAA (triethylamine acetate).

All reactions were run in an oven-dried round bottom flask, under argon atmosphere, and capped with a rubber septum. Anhydrous solvents were manipulated under an argon atmosphere with oven-dried syringes. As used herein, the term "aqueous workup" refers to a purification method comprising the following steps: (i) adding a reaction mixture to a saturated aqueous $NH_4Cl$ solution, a 5% HCl solution, or a saturated $Na_2S_2O_3$ solution, (ii) extracting the solution three times with an organic solvent, e.g., EtOAc, or $CH_2Cl_2$, (iii) washing the combined organic layer once with saturated NaCl, (iv) drying the solution with $Na_2SO_4$, (v) filtering the drying agent, and (vi) removing the solvent in vacuo. 3-Methoxy-1-hydroxynapthalene 1 was synthesized from 1,3-dihydroxynapthalene by the method of K. H. Bell and L. F. McCaffery (Aust. J. Chem. 46: 731 (1993)). 1-Amino-3-methoxynapthalene 18 was synthesized according the procedure of G. T. Morgan and E. D. Evans (J. Chem. Soc. 115: 1126 (1919)).

Example 1

Synthesis of 1-Diethylamino-3-Hydroxynapthalene 4 (FIG. 1)

3-methoxy-1-hydroxy napthalene 1 (1 gm) was suspended in dry $CH_2Cl_2$ (30 mL). Dry triethylamine (1.2 equivalents) was added and the reaction was cooled to −5° C. Trifluoromethanesulfonic anhydride (1.1 equivalents) suspended in $CH_2Cl_2$ (15 mL) was added dropwise with vigorous stirring over a period of 2 hours. The reaction was allowed to come to room temperature and subjected to aqueous work up using 5% HCl and $CH_2Cl_2$. The resulting crude 3-methoxynapthalene-1-triflate 2 was purified by normal phase flash chromatography employing an EtOAc/Hexane (1:10) mobile phase.

The purified 3-methoxynapthalene-1-triflate 2 was converted to the 1-diethylamino-3-methoxynapthalene 3 using the palladium-catalyzed triflate/amine coupling procedure of Wolfe as follows (J. P. Wolfe and S. L. Buchwald, JOC, 61: 1133 (1996)). The 3-methoxy-napthalene-1-triflate 2 (1 gram) was suspended in 100 mL of dry toluene with 0.015 equivalents of (S)-(−)-2,2'-bis(diphenylphosphino)-1,1'-binapthyl (BINAP), 0.005 equivalents of tris (dibenzylideneacetone)dipalladium ($Pd_2(dba)_3$), and 3 equivalents of dry diethyl amine. The reaction was purged with argon, and 3.3 equivalents of solid sodium t-butoxide was added with stirring. The reaction was then heated, and stirred for 16 hours at 80° C. in an oil bath. The reaction was allowed to come to room temperature and subjected to aqueous work up using 5% HCl and $CH_2Cl_2$ resulting in a crude 1-diethylamino-3-methoxynapthalene 3, which was purified by normal phase flash chromatography employing EtOAc:hexane (1:49) as the mobile phase ($^1$HNMR: $CD_3Cl$ d 8.20 (broad d, 1 H, J=9 Hz), 7.72(broad d, 1 H, J=7.8 Hz), 7.43 (dt, 1 H, J=7.2, 1.2 Hz), 7.34 (dt, 1 H, J=7.7, 1.2 Hz), 6.88 (d, 1 H, J=2.4 Hz), ), 6.82 (d, 1 H, J=2.4 Hz), 3.93 (s, 3 H), 3.21 (q, 4 H, J=7.2 Hz), 1.08 (t, 6 H, J=7.2 Hz)).

Next, the methyl group of the 1-diethyl-amino-3-methoxy-napthalene 3 was removed by boron tribromide deprotection as follows. The 1-amino-3-methoxy-napthalene (100 mg) was suspended in dry $CH_2Cl_2$ (5 mL) and the mixture was cooled to −70° C. in a dry ice/acetone bath. Boron tribromide (10 equivalents) was added dropwise and the reaction was stirred for 30 minutes, then placed in a refrigerator (0° C.) overnight. The reaction was quenched at −70° C. by careful addition of MeOH (10 mL). Solid $NaHCO_3$ (30 equivalents) was added and the reaction was warmed to room temperature, then briefly heated to reflux. The mixture was cooled and filtered, the filtrate was acidified with AcOH, and the solvent was removed in vacuo to give the crude 1-diethylamino-3-hydroxynapthalene 4, which was purified by normal phase flash chromatography employing EtOAc:hexane (1:4) as the mobile phase.

Example 2

Synthesis of N-Phenyl-3,3-Dimethyl-Hydroxy-Benzoindoline 9 (FIG. 1)

The 3-methoxynapthalene-1-triflate 2 was derivatized with aniline according to the palladium catalyzed triflate/ amine coupling reaction described above in Example 1 to give the 1-anilino-3-methoxynapthalene 5.

The 1-anilino-3-methoxynapthalene 5 was acetylated by an amino group acetylation procedure as follows. The 1-amino-3-methoxynapthalene 5 (500 mg) and 1.2 equivalents of dry Et$_3$N were suspended in 10 mL of dry CH$_2$Cl$_2$ and cooled to −5° C. using an ice/NaCl bath. 1.1 equivalent of 2-bromo-2-methylpropionylchloride was added dropwise and the reaction was stirred for 1 hour at −5° C. and stirred at room temperature for an additional 1 hour. The reaction was allowed to come to room temperature and subjected to aqueous work up using 5% HCl and EtOAc resulting in the crude intermediate 1-(bromoalkyl)amido-3-methoxy-napthalene 6, which was purified by normal phase flash chromatography employing EtOAc:hexane (1:9) as the mobile phase.

The 1-(bromoalkyl)amido-3-methoxy-napthalene 6 was cyclized using an AlCl$_3$ catalyzed Friedel-Crafts cyclization procedure as follows. 1 to 3 equivalents of AlCl$_3$ in nitrobenzene was added to the 1-(bromoalkyl)amido-3-hydroxy-napthalene 6. The reaction was heated to 130° C. and reacted for 1 hour. Aqueous work-up using NH$_4$Cl and EtOAc gave the crude N-phenyl-benzoindolinone intermediate 7, which was purified by normal phase flash chromatography employing EtOAc:hexane (1:4) as the mobile phase. The amide carbonyl group of the N-phenyl-benzoindoline intermediate 7 was then reduced with LAH to give compound 8 ($^1$HNMR: CD$_3$Cl d 7.71 (d, 1 H, J=7.8 Hz), 7.32 (m, 2 H), 7.24 (m, 2 H), 7.07 (bt, 1 H, J=6.6 Hz), 6.96 (m, 3 H), 6.84 (s, 1 H), 3.97 (s, 3 H), 3.92 (s, 2 H), 1.44 (s, 6 H).

Methoxy group deprotection of compound 8 was effected using the boron tribromide deprotection procedure described in Example 1, resulting in the N-phenyl-3,3-dimethyl-hydroxy-benzoindoline 9.

Example 3

Synthesis of N-Methyl-5-Hydroxy-(Tetrahydro) benzoquinoline 15 (FIG. 2)

Compound 10 was synthesized by condensation of methoxy-napthaldehyde and malonic acid employing piperidine catalysis in pyridine. Compound 10 was reduced with hydrogen over 10% Pd/carbon, followed by LAH reduction, and reacted as outlined for the synthesis of compound 2 above with trifluoromethanesulfonic anhydride to give the triflate 11. Triflate 11 was then reacted with NaN$_3$ (3 equiv.) in DMF at 100° C. for 6 hours. Then, the reaction was allowed to come to room temperature and subjected to aqueous work up using pure water and EtOAc resulting in pure compound 12. Compound 12 was suspended in dry CH$_2$Cl$_2$, complexed with 3 to 5 equivalents of solid AlCl$_3$, and refluxed for 2 hours yielding compound 13.

Compound 13 was alkylated with MeI according to a general amino group alkylation procedure as follows. The 3-methoxybenzoquinoline derivative (100 mg) 13 was suspended in 5 mL of dry THF and cooled to −5° C. (ice/NaCl). 1.1 equivalents of n-butyl lithium (1 M) was added dropwise, and the reaction was stirred for 1 hour. 3 equivalents of the MeI alkylating agent was added slowly and the reaction was allowed to stir at room temperature for 2 hours. Aqueous work-up using NH$_4$Cl and EtOAc gave a crude alkylated 3-methoxybenzoquinoline intermediate 14. Intermediate 14 was then purified by normal phase flash chromatography employing EtOAc:hexane (1:19) as the mobile phase ($^1$HNMR: CD$_3$Cl d 8.1 (broad d, 1 H, J=8.1 Hz), 7.68(dd, 1 H, J=8.1, 1.8 Hz), 7.34 (m, 2 H), 6.8 (s, 1 H), 3.92 (s, 3 H), 3.21 (m, 2 H), 2.94 (s, 3 H), 2.77 (t, 2 H, J=6.6 Hz), 1.92 (m, 2 H)). Subsequent methoxy group deprotection by the general boron tribromide procedure described above in Example 1 resulted in the N-methyl-hydroxybenzoquinoline derivative 15.

Example 4

Synthesis of 3-(5-Hydroxybenzoquinolin-1-yl) Propanesulfonic Acid 17 (FIG. 2)

Compound 13 was synthesized according to the procedure outlined above in Example 3 for the synthesis of the N-methyl-hydroxybenzoquinoline derivative 15. Compound 13 was then alkylated according to the general amino group alkylation procedure described above in Example 3, this time using 1,3-propane sultone as the alkylating agent rather than MeI, to give a 5-methoxybenzoquinoline-N-propanesulfonic acid intermediate 16 ($^1$HNMR: CD$_3$OD d 7.94 (d, 1 H, J=8.7 Hz), 7.65 (d, 1 H, J=8.4 Hz), 7.32 (t, 1 H), 7.27 (t, 1 H), 6.85 (s, 1 H), 4.89 (s, 3 H), 3.20 (m, 2 H), 3.08 (bt, 2 H, J=6 Hz), 2.91 (m, 2 H), 2.72 (t, 2 H, J=6.6 Hz), 2.33 (m, 2 H), 1.89 (m, 2 H). Subsequent methoxy group deprotection of compound 16 by the general boron tribromide procedure described above in Example 1 resulted in the 3-(5-hydroxybenzoquinolin-1-yl) propanesulfonic acid 17.

Example 5

Synthesis of N-Methyl-2,2,4-Trimethyl-5-Hydroxy-(Tetrahydro)benzoquinoline 22 (FIG. 3)

Following the procedure of A. Rosowsky and E. J. Modest (J.O.C., 30: 1832 (1965)), 1-amino-3-methoxynapthalene 18 (1 gm) was dissolved in dry acetone (50 mL), and 0.01 equivalent of iodine was added to the solution. The reaction was heated and stirred for 16 hours, cooled, and then quenched with saturated Na$_2$S$_2$O$_3$. The reaction mixture was then subjected to aqueous work up using saturated Na$_2$S$_2$O$_3$ and EtOAc resulting in the crude methoxybenzoquinoline 19. The methoxybenzoquinoline 19 was purified by flash chromatography using an EtOAc/hexane 1:9 mobile phase. Compound 19 was then alkylated with MeI according to the general amino group alkylation procedure described above in Example 3 to give compound 20. Compound 20 was reduced with H$_2$ in a Parr hydrogenator at 70 psi and 10% Pd/C catalysis to give a N-methyl-2,2,4-trimethyl-5-methoxybenzoquinoline intermediate 21 ($^1$HNMR: CD$_3$Cl d 8.20 (bd, 1 H, J=7.5 Hz), 7.65 (bd, 1 H, J=7.5 Hz), 7.33 (m, 2 H), 6.89 (s, 1 H), 3.94 (s, 3 H), 3.14 (b sextet, 1 H, J=6.6 Hz), 2.80 (3, 3 H), 1.89 (d, 2 H, J=8.7), 1.42 (d, 3 H, J=6.9 Hz), 1.34 (s, 3 H), 1.05 (s, 3 H). Subsequent methoxy group deprotection of compound 21 by the general boron tribromide procedure described above in Example 1 gave the N-methyl-5-hydroxy-(tetrahydro)benzoquinoline 22.

Example 6

Synthesis of N-Methyl-3,3-Dimethyl-4-Hydroxy-Benzoindoline 27 (FIG. 3)

1-Amino-3-methoxynapthalene 18 was acetylated with 2-bromo-2-methylpropionyl chloride according to the general amino group acylation procedure described above in Example 2 to give compound 23. Compound 23 was cyclized by the Friedel-Crafts cyclization procedure described above in Example 2 to give compound 24. Next, compound 24 was reduced with 3 equivalents LAH in THF to give the 4-methoxybenzoindoline 25. Compound 25 was alkylated using the general amino group alkylation procedure described above in Example 3 using methyl iodide as the alkylating agent to give a N-methyl-3,3-dimethyl-4-methoxybenzoindoline intermediate 26 ($^1$HNMR: CD$_3$Cl d 8.07 (bd, 1 H, J=8.4 Hz), 7.69 (bd, 1 H, J=8.1 Hz), 7.33 (bt, 1 H, J=7.8 Hz), 7.22 (bt, 1 H, J=8.1 Hz), 6.70 (s, 1 H), 3.92 (s, 3 H), 3.32 (s, 2 H), 3.32 (s, 3 H), 1.44 (s, 6 H). Subsequent methoxy group deprotection of compound 26 by the general boron tribromide procedure described in Example 1 resulted in the N-methyl-3,3-dimethyl-4-hydroxy-benzoindoline 27.

Example 7

Synthesis of N-Ethyl-3,3-Dimethyl-4-Hydroxy-Benzoindoline 29 (FIG. 3)

The 4-methoxybenzoindoline 25 was synthesized as described above in Example 6. Compound 25 was alkylated by the general amino group alkylation procedure described in Example 3 employing ethyl iodide as the alkylating agent to give the N-ethyl-3,3-dimethyl-4-methoxybenzoindoline intermediate 28 ($^1$HNMR: CD$_3$Cl d 7.90 (d, 1 H, J=8.7 Hz), 7.68 (d, 1 H, J=8.1 Hz), 7.32 (bt, 1 H, J=7.5 Hz), 7.22 (bt, 1 H, J=6.9 Hz), 6.69 (s, 1 H), 3.83 (s, 3 H), 3.52 (q, 2 H J=7.5 Hz), 3.38 (s, 2 H), 1.46 (s, 6 H), 1.27 (t, 3 H, J=7.5 Hz). Subsequent methoxy group deprotection of compound 28 by the general boron tribromide procedure described in Example 1 yielded the N-ethyl-3,3-dimethyl-4-hydroxy-benzoindoline 29.

Example 8

Synthesis of Selected Dibenzorhodamine Dye Compounds

Figure 5:
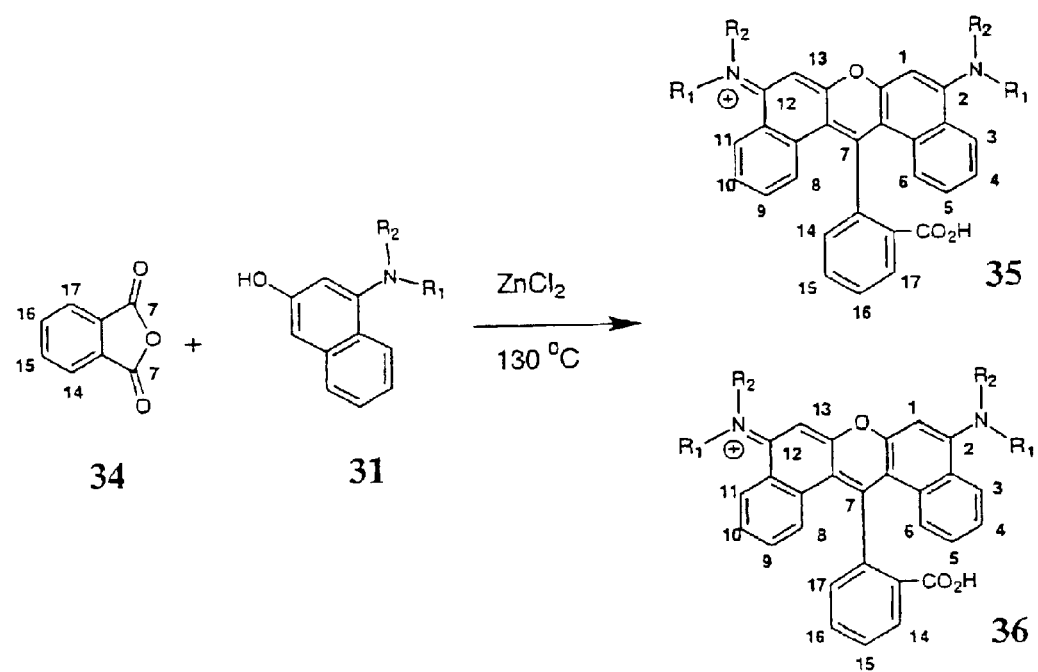
FIGS. 5 and 6 show exemplary synthetic pathways for the synthesis of the dibenzorhodamine dye compounds of the invention.

General Procedure A (FIG. 5). A solid phthalic anhydride derivative 34 was mixed with 1.4 equivalents of an aminohydroxy intermediate 31 and 2.8 equivalents of ZnCl$_2$. The oven dried reaction vessel was capped with a rubber septa and purged with Argon. The solid mixture was heated briefly at 130° C. until melting was observed, e.g., after approximately 15 minutes. 1,2-Dichlorobenzene (approximately 10 equivalents) was added by syringe to the reaction mixture, and the heterogeneous mixture was heated to 130° C. to 170° C. for 4 hours. The crude reaction mixture was cooled, suspended in a minimal amount of MeOH:CH$_2$Cl$_2$ (1:19), loaded directly onto a normal phase flash chromatography column, and the crude dye was eluted with an MeOH:CH$_2$Cl$_2$ (1:19) mobile phase. When necessary, the dye was purified and separated into distinct isomers 35 and 36 by PTLC developed with MeOH:CH$_2$Cl$_2$ (1:9). The isomerically pure dye, which migrated as a single spot on silica TLC eluting with 1:9 MeOH:CH$_2$Cl$_2$, was identified by its UV/Visible absorption spectra and its long wavelength fluorescent excitation and emission spectra.

General Procedure B (FIG. 6). In the general procedure outlined in FIG. 6, a solid phthalic anhydride derivative 34 (100 mg) was placed in a round bottom flask capped with a rubber septa and purged with dry argon. Dry nitrobenzene (2 mL) was added and heated to dissolve the anhydride. The mixture was cooled to room temperature and 3 to 6 equivalents of anhydrous AlCl$_3$ was added with stirring to dissolve the solid. Subsequently, 1 equivalent of a 1-amino-3-methoxynapthalene intermediate 31 was added with stirring and the reaction was heated to 130° C. for 1 hour. The reaction was then cooled and suspended in EtOAc. The organic layer was washed with saturated NH$_4$Cl and brine, dried over Na$_2$SO$_4$, filtered, and the solvent was removed in vacuo. When necessary, the resulting ketone intermediate 37/38 was purified and separated into distinct isomers 37 and 38 using normal phase flash chromatography using (MeOH:CH$_2$Cl$_2$, 1:19) as the mobile phase, or by recrystallization. The methoxy group of the isomerically pure intermediate 37 or 38 was removed according to the general boron tribromide deprotection procedure described in Example 1 to give amino-hydroxynapthalene ketone 39. The amino-hydroxynapthalene ketone 39 (100 mg) was then reacted at 130° C. with 1 equivalent of a 1-amino-3-napthalene intermediate 32 in dry 1,2-dichlorobenzene (2 mL) for 2 hours. The reaction was cooled, giving isomerically pure and asymmetrically substituted product 40 that was purified as in General Procedure A above.

Synthesis of Dibenzorhodamine Dye 41 (FIG. 7). General procedure A was followed employing dichlorotrimellitic anhydride as the phthalic anhydride derivative, i.e., compound 34 where the substituents at C-14 and C-17 are Cl and the substituent at C-15 is CO$_2$H, and 1-diethylamino-3-hydroxynapthalene 4 as the aminohydroxy intermediate 31.

Synthesis of Dibenzorhodamine Dye 42 (FIG. 7). General procedure A was followed employing dichlorotrimellitic anhydride as the phthalic anhydride derivative, i.e., compound 34 where the substituents at C-14 and C-17 are Cl and the substituent at C-15 is CO$_2$H, and N-methyl-5-hydroxy-benzoquinoline 15 as the aminohydroxy intermediate 31.

Synthesis of Dibenzorhodamine Dye 43 (FIG. 7). General procedure A was followed employing dichlorotrimellitic anhydride as the phthalic anhydride derivative, i.e., compound 34 where the substituents at C-14 and C-17 are Cl and the substituent at C-15 is CO$_2$H, and 5-hydroxy-benzoquinoline 17 as the aminohydroxy intermediate 31.

Synthesis of Dibenzorhodamine Dye 44 (FIG. 7). General procedure A was followed employing dichlorotrimellitic anhydride as the phthalic anhydride derivative, i.e., compound 34 where the substituents at C-14 and C-17 are Cl and the substituent at C-15 is CO$_2$H, the N-methyl-2,2,4-trimethyl-5-hydroxy-benzoquinoline 22 as the aminohydroxy intermediate 31.

Syntesis of Dibenzorhodamine Dye 45 (FIG. 7). General procedure A was followed employing dichlorotrimellitic anhydride as the phthalic anhydride derivative, i.e., compound 34 where the substituents at C-14 and C-17 are Cl and the substituent at C-15 is CO$_2$H, and N-methyl-3,3-dimethyl-4-hydroxy-benzoindoline 27 as the aminohydroxy intermediate 31.

Syntesis of Dibenzorhodamine Dye 46 (FIG. 7). General procedure A was followed employing tetrafluorophthalic anhydride as the phthalic anhydride derivative, i.e., compound 34 where the substituents at C-14 to C-17 are F, and N-ethyl-3,3-dimethyl-4-hydroxy-benzoindoline 29 as the aminohydroxy intermediate 31.

Syntesis of Dibenzorhodamine Dye 47 (FIG. 7). General procedure A was followed employing dichlorotrimellitic anhydride as the phthalic anhydride derivative, i.e., compound 34 where the substituents at C-14 and C-17 are Cl and the substituent at C-15 is CO$_2$H, and N-phenyl-3,3-dimethyl-4-hydroxy-benzoindoline 9 as the aminohydroxy intermediate 31.

Example 9

Spectral Properties of Selected Dibenzorhodamine Dye Compounds

The following table presents important spectral properties of several representative dibenzorhodamine dye compounds of the invention. All spectra were recorded at room temperature, in 1×TBE buffer and 8 M urea, for the free dye having 0.05 absorption at the dye's $\lambda_{max,\ abs}$. Dye concentration was approximately $10^{-6}$ M.

| Dye | Absorption Maximum (nm) | Emission Maximum (nm) | Full Width at Half Max (nm) |
|---|---|---|---|
| 41 | 585 | 614 | 59 |
| 42 | 609 | 634 | 42 |
| 43 | 597 | 637 | 47 |
| 44 | 598 | 640 | 50 |
| 45 | 639 | 650 | 31 |
| 46 | 639 | 652 | 33 |
| 47 | 632 | 676 | 66 |

All publications, patents, and patent applications referred to herein are hereby incorporated by reference to the same extent as if each individual publication, patent or patent application was specifically and individually indicated to be incorporated by reference.

Although only a few embodiments have been described in detail above, those having ordinary skill in the chemical arts will clearly understand that many modifications are possible in these embodiments without departing from the teachings thereof. All such modifications are intended to be encompassed within the scope following claims.

We claim:

1. A method of polynucleotide sequencing comprising the steps of:

forming a mixture of a first, a second, a third, and a fourth class of polynucleotides such that:

each polynucleotide in the first class includes a 3'-terminal dideoxyadenosine and is labeled with a first dye;

each polynucleotide in the second class includes a 3'-terminal dideoxycytidine and is labeled with a second dye;

each polynucleotide in the third class includes a 3'-terminal dideoxyguanosine and is labeled with a third dye; and each polynucleotide in the fourth class includes a 3'-terminal dideoxythymidine and is labeled with a fourth dye;

wherein at least one of the first, second, third, or fourth dyes is a dibenzorhodamine compound comprising the structure

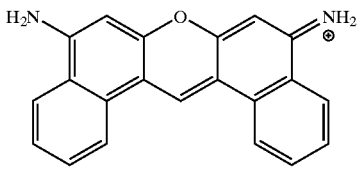

including nitrogen- and aryl-substituted forms thereof;

the other of the dyes being spectrally resolvable from the dibenzorhodamine dye(s) and from each other;

electrophoretically separating the polynucleotides thereby forming bands of similarly sized polynucleotides;

illuminating the bands with an illumination beam capable of causing the dyes to fluoresce; and identifying the classes of the polynucleotides in the bands by the fluorescence spectrum of the dyes.

2. The method of claim 1, wherein the step of electrophoretically separating is carried out in an electrophoretic matrix is uncrosslinked polyacrylamide or crosslinked polyacrylamide.

3. The method of claim 1, wherein the uncrosslinked polyacrylamide or crosslinked polyacrylamide has a concentration of from 2–20 weight percent.

4. The method of claim 1, wherein the uncrosslinked polyacrylamide or crosslinked polyacrylamide concentration is from 4–8 weight percent.

5. The method of claim 1, wherein the electrophoretic matrix comprises a denaturing agent selected from urea and formamide.

* * * * *